US008815559B2

(12) United States Patent
Jones et al.

(10) Patent No.: US 8,815,559 B2
(45) Date of Patent: Aug. 26, 2014

(54) AMYLASE FROM NESTERENKONIA AND METHODS OF USE, THEREOF

(75) Inventors: Brian E. Jones, Leidschendam (NL); Marc Kolkman, Oegstgeest (NL)

(73) Assignee: Danisco US Inc., Palo Alto, CA (US)

( * ) Notice: Subject to any disclaimer, the term of this patent is extended or adjusted under 35 U.S.C. 154(b) by 89 days.

(21) Appl. No.: 13/579,819

(22) PCT Filed: Jan. 20, 2011

(86) PCT No.: PCT/US2011/021884
§ 371 (c)(1),
(2), (4) Date: Mar. 28, 2013

(87) PCT Pub. No.: WO2011/102933
PCT Pub. Date: Aug. 25, 2011

(65) Prior Publication Data
US 2013/0177964 A1    Jul. 11, 2013

Related U.S. Application Data

(60) Provisional application No. 61/305,674, filed on Feb. 18, 2010.

(51) Int. Cl.
*C11D 3/386* (2006.01)
*C12Q 1/40* (2006.01)
*C12N 9/28* (2006.01)

(52) U.S. Cl.
CPC ................................. *C12N 9/2417* (2013.01)
USPC .......................................... 435/202; 435/22

(58) Field of Classification Search
None
See application file for complete search history.

(56) References Cited

U.S. PATENT DOCUMENTS

| | | | |
|---|---|---|---|
| 4,106,991 | A | 8/1978 | Markussen et al. |
| 4,435,307 | A | 3/1984 | Barbesgaard et al. |
| 4,661,452 | A | 4/1987 | Markussen et al. |
| 5,281,526 | A | 1/1994 | Good et al. |
| 5,457,046 | A | 10/1995 | Woldike et al. |
| 5,648,263 | A | 7/1997 | Schulein et al. |
| 5,686,593 | A | 11/1997 | Woldike et al. |
| 5,691,178 | A | 11/1997 | Schulein et al. |
| 5,763,254 | A | 6/1998 | Woldike et al. |
| 5,776,757 | A | 7/1998 | Schulein et al. |
| 2002/0182734 | A1 | 12/2002 | Diaz-Torres et al. |
| 2005/0003419 | A1 | 1/2005 | Breves et al. |
| 2010/0035787 | A1 | 2/2010 | Amin et al. |

FOREIGN PATENT DOCUMENTS

| | | |
|---|---|---|
| EP | 238216 | 2/1987 |
| EP | 218272 | 4/1987 |
| EP | 238023 | 9/1987 |
| EP | 258068 | 3/1988 |
| EP | 260105 | 3/1988 |
| EP | 305216 | 1/1989 |
| EP | 331376 | 6/1989 |
| EP | 407225 | 9/1991 |
| EP | 531315 | 11/1991 |
| EP | 0495257 | 7/1992 |
| GB | 1372034 | 10/1974 |
| GB | 1483591 | 8/1977 |
| WO | WO 89/06270 | 7/1989 |
| WO | WO 89/06279 | 7/1989 |
| WO | WO 89/09259 | 10/1989 |
| WO | WO 91/16422 | 10/1991 |
| WO | WO 91/17243 | 11/1991 |
| WO | WO 92/05249 | 2/1992 |
| WO | WO 92/06154 | 4/1992 |
| WO | WO 92/19708 | 11/1992 |
| WO | WO 92/19709 | 11/1992 |
| WO | WO 92/19729 | 11/1992 |
| WO | WO 93/24618 | 12/1993 |
| WO | WO 94/01541 | 1/1994 |
| WO | WO 94/07998 | 4/1994 |
| WO | WO 94/25578 | 11/1994 |
| WO | WO 94/25583 | 11/1994 |
| WO | WO 95/06720 | 3/1995 |
| WO | WO 95/10602 | 4/1995 |
| WO | WO 95/14783 | 6/1995 |
| WO | WO 95/22615 | 8/1995 |
| WO | WO 95/24471 | 9/1995 |
| WO | WO 95/30744 | 11/1995 |
| WO | WO 95/35381 | 12/1995 |
| WO | WO 96/00292 | 1/1996 |
| WO | WO 96/11262 | 4/1996 |
| WO | WO 96/12012 | 4/1996 |
| WO | WO 96/13580 | 5/1996 |
| WO | WO 96/27002 | 9/1996 |
| WO | WO 96/29397 | 9/1996 |
| WO | WO 97/04079 | 2/1997 |
| WO | WO 97/07202 | 2/1997 |
| WO | WO 98/08940 | 3/1998 |
| WO | WO 98/12307 | 3/1998 |
| WO | WO 98/15257 | 4/1998 |
| WO | WO 98/20115 | 5/1998 |
| WO | WO 98/20116 | 5/1998 |
| WO | WO 98/34946 | 8/1998 |

(Continued)

OTHER PUBLICATIONS

Martins, Rita E., "Starch-hydrolizing bacteria from Ethiopian soda lakes," *Extremophiles* (2001) 51:135-144.
Notification of Transmittal of the International Search Report and the Written Opinion of the International Authority for PCT/US2011/021884, 13 pages total, May 17, 2011.
Cayot and Tainturier, (1997) *Anal. Biochem.* 249:184-200.
Conti, Monica M. et al., *J. Chromatography A* (1997) 757:237-245.
Dartois et al., *Biochemica et Biophysica Acta*, (1992) 1131:253-360.

(Continued)

*Primary Examiner* — Suzanne M Noakes
*Assistant Examiner* — Gerard Lacourciere
(74) *Attorney, Agent, or Firm* — Danisco US Inc.

(57) ABSTRACT

Compositions and methods relating to an alpha-amylase enzyme obtained from *Nesterenkonia* and related spp. are described.

19 Claims, 9 Drawing Sheets

(56) References Cited

FOREIGN PATENT DOCUMENTS

| WO | PCT/DK98/00299 | 1/1999 |
|----|----|----|
| WO | WO 01/14629 | 3/2001 |
| WO | WO 01/34899 | 5/2001 |
| WO | WO 02/14490 | 2/2002 |
| WO | WO 2005/056783 | 6/2005 |
| WO | WO2008088493 | 7/2008 |

OTHER PUBLICATIONS

Duckworth et al., *FEMS Microbiology Ecology* (1996) 19:181-91.
Lynch et al., (2006) GenBank Accession No. DQ058731. 3 pages.
Hage et al. *Nature* (1994) 369:637-639.
Kaushik, J.K. et al., *Journal of Biol. Chem.* (2003) 278:26458-65.
McKenzie et al., *Plasmid* (1986) 15:93-103.
Neidhardt et al. *Journal of Bacteriology* (1974) 119:736-47.
Prakash, B. et al., "Production, purification, and characterization of two extremely halotolerant, thermostable, and alkali-stable alpha-amylases from *Chromohalobacter* sp. TVSP 101," *Process Biochemistry* (2009) 44(2) 210-215.
Shafiei M. et al., "Purification and biochemical characterization of a novel SDS and surfactant stable, raw starch digesting, and halophilic alpha-amylase from a moderately halophilic bacterium, Nesterenkonia sp. strain F." (2010) *Process Biochemistry* 45(5) 694-699.
Solingen et al., (2001) *Extremophiles* 5:333-41.
Stackebrandt, E. et al., *Int. J. Syst. Bacteriol.* (1995) 44:682-92.
Sumitani, J. et al., "New type of starch-binding domain: the direct repeat motif in the C-terminal region of *Bacillus* sp. No. 195 a-amylase contributes to starch binding and raw starch degrading," *Biochem J.* (2000) 350:477-484.
Wen-Jun, Li et al., "Nesterenkonia halotolderans sp. nov. And Nesterenkonia xinjiangensis sp. nov., actinobacteria from saline soils in the west of China," (2004) *International Journal of Systematic and Evolutionary Microbiology* 54(3) 837-841.

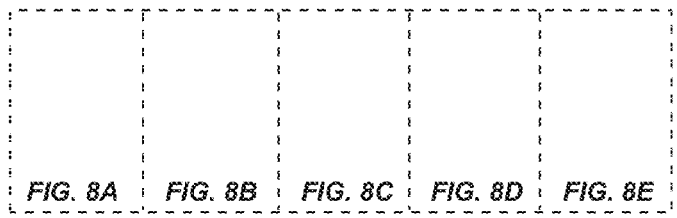

FIG. 8

SEQ ID NO: 1: Partial nucleotide sequence of the *Nesterenkonia xinjiangensis* B4.2S6 16S rRNA gene.
CGTGCTTGCA CGGGTGGATT AGTGGCGAAC GGGTGAGTAT CACGTGAGTA
ACCTGCCCTT GACTCTGGGA TAAGCCTGGG AAACTGGGTC TAATACCGGA
TGCGACCAGT CCCCGCATGG GGTGCTGGTG GAAAGATTTT ATCGGTCTTG
GATGGACTCG CGGCCTATCA GCTAGACGGT GGGGTAGAAG CCCACCGTGG
CGATGACGGG TAGCCGGCCT GAGAGGGTGA CCGGCCACAC TGGGACTGAG
ACACGGCCCA GACTCCTACG GGAGGCAGCA GTGGGGAATA TTGCACAATG
GGCGCAAGCC TGATGCAGCG ACGCCGCGTG CGGGATGACG GCCTTCGGGT
TGTAAACCGC TTTCAGCAGG GAAGAAGCTT TATTGTGACG GTACCTGCAG
AAGAAGCGCC GGCTAACTAC GTGCCAGCAG CCGCGGTAAT SEQ ID NO: 2: Nucleotide sequence of primer pRANGER-FW.
CATAAGATTAGCGGATCCTACCTG SEQ ID NO: 3: Nucleotide sequence of primer pRANGER-RV.
CAGCTTGTCCAGCAGGGTTGTCCAC SEQ ID NO: 4: Nucleotide sequence of primer Nest-Insert3-RV.
GTGAGGTCTGCACATAGCCGTAAC SEQ ID NO: 5: Nucleotide sequence of primer Nest-Insert3-FW.
GTACTGCAACGTCTACACCGGCTC SEQ ID NO: 6: Nucleotide sequence of primer Nest-add.-Fw.
GGAATGCGACCTGCTCGGACTCG

FIG. 8A

SEQ ID NO: 7: Nucleotide sequence of the *Nesterenkonia xinjiangensis* B4.2S6 alpha-amylase gene.

gtgcggacggcaggggctctcggactggccggtgccatgctggcacccgccaccatgcctgcggc
cacccgccttcgacggcgggcccccggcctccgacaaggcggccgatcaccgccggcgcccgcggcg
cggagaacgcctcgcagaactccgccaccacaccgaccggctcccggagctccgcaccgcggcg
cagagcgcggaggggacgaaggacaccaccgccgtgatgttccagtggacgtggaacagcatcgc
ccgcgaatgccgtgagacgctcggcccggccggttacggctatgtgcagacctcaccggcccagg
agcacatccacggtgagccgtggtggacccactatcagccggtgagctaccagatcgaatctcgc
ctgggtacccgcgacgagttcgcggacatggtctccacctgcaacgacgccggcgtgaaggtcat
cgccgacgtcgtcatcaaccacatgacgggacaggacgagggcgtgggttgggccggcagcgagt
tcacccacacgaactatccggcacctactccccgacgacttccacaaccacggctgcgaggtg
gaggactacaccgaccgctggcaagtccaggaatgcgacctgctcggactcgccgatctgaagac
cagctccgactacgtccagtcgcggatcggcgaacacctcgaggacctcatcgacctcggcgtcg
agggcttccgcatcgatgcggtcaagcacatctccgccgacgacctcaccggcatcctggaccgt
gtggacctgaccgacatctacgtggtctccgaggtcatccgcggcggcggcgaacccatccagcc
cgaggagtaccagcacctgggcgacgtccacgaattcacctggggccggaagctcaaagaggcct
tcgacggcggcgacatccactggctgctctccggcgagggcatcggtgagcctgggaaggcttc
atcgccgacgagcacgccggcaccttcgtggacaaccacgacaccgaacgcaacggcgagaccct
gagctacaaggacggggacgcctaccgcctggcccaggccttcacgctggcctggccgtacggca
tgcccgcggtgcactccggctactcgttcagcgactacgacgccggccccgtgcagcatgaggac
ggtcggatccgcgacgcggtctgcggcgaggagaactggacctgcatccacgcccagaccgaggt
ggccaacatggtcgggttccgcaacgccgtcggggacgcccggtgaccgacacgtggaccaacg
actcccacgccctggccttcggccgtggcgaccagggcttcctggtggccaaccgcggaccgaac
agtgtgcagcacacctggcagacctccttgccggccggcgagtactgcaacgtctacaccggctc
cgccacgtccgagggttgctccggggaaaccgtgaccgtggcggccgacggcaccttcagcgccc
acgtgggcccggactccgccgtggctctgcacgtgggcgccaccccggccagcggcgacggagac
ggcgacggtgacggatcgacgccgccggaggagcgcgagctgtccctgttctacgccaccgactg
ggagaccccgcacgtccactaccaggtgggcgacggcgagtggacggacctgccggcctggcca
tgaccgaggcctgcgagggatggttccacgccgagatcgacctcggcacggccggaccatcacc
gcggcattcaacgacggcggcgacgctggacaacaacgacggtgaggactacacgatcggctc
cggcgtcatccaggtctcggacagccagctggccgagggcgacccctgcgaggccaacccgcc
cgggcgaggacccgacctgaccgtgtactacgagaccggctgggagaacccgcgcattcactac
caggagggcgacggcggctggacggacgttccgggtgtggcaatggccgaggcctgtgagggctg
gttccggggcggacatccagctcgacgacgcggacggcatcaccgcggccttcaacgacggcgccg
gcacctgggacaacaacgaccatcaggactacagcatcgccgccggcgagcagcaagtgtcagga
ggcgaggtcactgcaggcaacccctgt

*FIG. 8B*

SEQ ID NO: 8: Nucleotide sequence encoding the *Nesterenkonia xinjiangensis* B4.2S6 alpha-amylase mature protein.

ttcgacggcgggccccggcctccgacaaggcggccgatcacgccggcgccgcggcgcggagaa
cgcctcgcagaactccgccaccacaccgaccggctcccggagctccgcaccgcggcgcagagcg
cggaggggacgaaggacaccaccgccgtgatgttccagtggacgtggaacagcatcgcccgcgaa
tgccgtgagacgctcggccggccggttacggctatgtgcagacctcaccggcccaggagcacat
ccacggtgagccgtggtggacccactatcagccggtgagctaccagatcgaatctcgctgggta
cccgcgacgagttcgcggacatggtctccacctgcaacgacgccggcgtgaaggtcatcgccgac
gtcgtcatcaaccacatgacgggacaggacgagggcgtgggttgggccggcagcgagttcaccca
cacgaactatccggcacctactccccgacgacttccacaaccacggctgcgaggtggaggact
acaccgaccgctggcaagtccaggaatgcgacctgctcggactcgccgatctgaagaccagctcc
gactacgtccagtcgcggatcggcgaacacctcgaggacctcatcgacctcggcgtcgagggctt
ccgcatcgatgcggtcaagcacatctccgccgacgacctcaccggcatcctggaccgtgtggacc
tgaccgacatctacgtggtctccgaggtcatccgcggcggcggcgaacccatccagcccgaggag
taccagcacctgggcgacgtccacgaattcacctggggccggaagctcaaagaggccttcgacgg
cggcgacatccactggctgctctccggcgagggcatcggtgagacctgggaaggcttcatcgccg
acgagcacgccggcaccttcgtggacaaccacgacaccgaacgcaacggcgagaccctgagctac
aaggacggggacgcctaccgcctggcccaggccttcacgctggcctggccgtacggcatgccgc
ggtgcactccggctactcgttcagcgactacgacgccggccccgtgcagcatgaggacggtcgga
tccgcgacgcggtctgcggcgaggagaactggacctgcatccacgcccagaccgaggtggccaac
atggtcgggttccgcaacgccgtcggggacgccccggtgaccgacacgtggaccaacgactccca
cgccctggccttcggccgtggcgaccagggcttcctggtggccaaccgcggaccgaacagtgtgc
agcacacctggcagacctccttgccggccggcgagtactgcaacgtctacaccggctccgccacg
tccgagggttgctccggggaaaccgtgaccgtggcggccgacggcaccttcagcgccacgtggg
cccggactccgccgtggctctgcacgtgggcgccaccccggccagcggcgacggagacggcgacg
gtgacggatcgacgccgcggaggagcgcgagctgtccctgttctacgccaccgactgggagacc
ccgcacgtccactaccaggtgggcgacgcgagtggacggacctgcccggcctggccatgaccga
ggcctgcgagggatggttccacgccgagatcgacctcggcacggcccggaccatcaccgcggcat
tcaacgacggcggcgacgcctgggacaacaacgacggtgaggactacacgatcggctccggcgtc
atccaggtctcggacagccagctggccgagggcgaccctgcgaggccaacccgccccgggcga
ggaccccgacctgaccgtgtactacgagaccggctgggagaacccgcgcattcactaccaggagg
gcgacggcggctggacggacgttccgggtgtggcaatggccgaggcctgtgagggctggttccgg
gcggacatccagctcgacgacgcggacggcatcaccgcggccttcaacgacggcgccggcacctg
ggacaacaacgaccatcaggactacagcatcgccgccggcgagcagcaagtgtcaggaggcgagg
tcactgcaggcaaccctgt

*FIG. 8C*

SEQ ID NO: 9: Amino acid sequence of the *Nesterenkonia xinjiangensis* B4.2S6 alpha-amylase precursor protein, including the 24-amino acid signal sequence (bold typeface).

```
  1  MRTAGALGLA GAMLAPATMP AATAFDGGPP ASDKAADHAG ARGAENASQN
 51  SAHHTDRLPE LRTAAQSAEG TKDTTAVMFQ WTWNSIAREC RETLGPAGYG
101  YVQTSPAQEH IHGEPWWTHY QPVSYQIESR LGTRDEFADM VSTCNDAGVK
151  VIADVVINHM TGQDEGVGWA GSEFTHTNYP GTYSPDDFHN HGCEVEDYTD
201  RWQVQECDLL GLADLKTSSD YVQSRIGEHL EDLIDLGVEG FRIDAVKHIS
251  ADDLTGILDR VDLTDIYVVS EVIRGGGEPI QPEEYQHLGD VHEFTWGRKL
301  KEAFDGGDIH WLLSGEGIGE TWEGFIADEH AGTFVDNHDT ERNGETLSYK
351  DGDAYRLAQA FTLAWPYGMP AVHSGYSFSD YDAGPVQHED GRIRDAVCGE
401  ENWTCIHAQT EVANMVGFRN AVGDAPVTDT WTNDSHALAF GRGDQGFLVA
451  NRGPNSVQHT WQTSLPAGEY CNVYTGSATS EGCSGETVTV AADGTFSAHV
501  GPDSAVALHV GATPASGDGD GDGDGSTPPE ERELSLFYAT DWETPHVHYQ
551  VGDGEWTDLP GLAMTEACEG WFHAEIDLGT ARTITAAFND GGDAWDNNDG
601  EDYTIGSGVI QVSDSQLAEG DPCEAQPAPG EDPDLTVYYE TGWENPRIHY
651  QEGDGGWTDV PGVAMAEACE GWFRADIQLD DADGITAAFN DGAGTWDNND
701  HQDYSIAAGE QQVSGGEVTA GNPC
```

SEQ ID NO: 10: Amino acid sequence of the *Nesterenkonia xinjiangensis* B4.2S6 alpha-amylase signal peptide.
MRTAGALGLA GAMLAPATMP AATA SEQ ID NO: 11: Amino acid sequence of the *Nesterenkonia xinjiangensis* B4.2S6 alpha-amylase mature protein.

```
  1  FDGGPPASDK AADHAGARGA ENASQNSAHH TDRLPELRTA AQSAEGTKDT
 51  TAVMFQWTWN SIARECRETL GPAGYGYVQT SPAQEHIHGE PWWTHYQPVS
101  YQIESRLGTR DEFADMVSTC NDAGVKVIAD VVINHMTGQD EGVGWAGSEF
151  THTNYPGTYS PDDFHNHGCE VEDYTDRWQV QECDLLGLAD LKTSSDYVQS
201  RIAEHLEDLI DLGVEGFRID AVKHISADDL TGILDRVDLT DIYVVSEVIR
251  GGGEPIQPEE YQHLGDVHEF TWGRKLKEAF DGGDIHWLLS GEGIGETWEG
301  FIADEHAGTF VDNHDTERNG ETLSYKDGDA YRLAQAFTLA WPYGMPAVHS
351  GYSFSDYDAG PVQHEDGRIR DAVCGEENWT CIHAQTEVAN MVGFRNAVGD
401  APVTDTWTND SHALAFGRGD QGFLVANRGP NSVQHTWQTS LPAGEYCNVY
451  TGSATSEGCS GETVTVAADG TFSAHVGPDS AVALHVGATL ASGDGDGDGD
501  GSTPPEEREL SLFYATDWET PHVHYQVGDG EWTDLPGLAM TEACEGWFHA
551  EIDLGTARTI TAAFNDGGDA WDNNDGEDYT IGSGVIQVSD SQLAEGDPCE
601  AQPAPGEDPD LTVYYETGWE NPRIHYQEGD GGWTDVPGVA MAEACEGWFR
651  ADIQLDDADG ITAAFNDGAG TWDNNDHQDY SIAAGEQQVS GGEVTAGNPC
```

FIG. 8D

SEQ ID NO: 12: Amino acid sequence of carbohydrate binding module CBM 25(1).
```
  1  FYATDWETPH VHYQVGDGEW TDLPGLAMTE ACEGWFHAEI DLGTARTITA
 51  AFNDGGDAWD NNDGEDYTIG SGVIQVSDSQ LAEG
```

SEQ ID NO: 13: Amino acid sequence of carbohydrate binding module CBM 25(2).
```
  1  YYETGWENPR IHYQEGDGGW TDVPGVAMAE ACEGWFRADI QLDDADGITA
 51  AFNDGAGTWD NNDHQDYSIA AGEQQVSGGE VTAG
```

SEQ ID NO: 14: Nucleotide sequence of primer pHPLT-AmyNest-Fw.
CTCATTCTGCAGCTTCAGCAGCTGCGGAGGGGACGAAGGACACCACC

SEQ ID NO: 15: Nucleotide sequence of primer pHPLT-AmyNest-Rv.
GTCCTCTGTTAACTCAACAGGGGTTGCCAGCAGTGACCTCG

SEQ ID NO: 16: Nucleotide sequence of primer pHPLT-F1.
TACATATGAGTTATGCAGTTTG

SEQ ID NO: 17: Nucleotide sequence of primer pHPLT-R1.
GTTATGAGTTAGTTCAAATTCG

SEQ ID NO: 18: Amino acid sequence of the immature form of *Bacillus* sp. 195 alpha-amylase.
MPALYQGVIADVRAKRKRLQVLAKMVLIALLGTLLSATAFAAPASAAAPGPKDATAVMFS
WTWNAIARECTENLGPAGYGYVQTSPPQEHIQGAAWWTHYQPVSYKIESRFGTRAEFKAM
VDTCHAAGVKVIADAVINHMTGQSAGGTGWAGSTFQHYDYPGIYQSQDFHSCRRNIANYQ
DRWEVQECNLVNLADLNTSSSYVQGKIAAYLNDLVSLGVDGLRIDAVKHIAASDMQGILS
KVNDRARLYIVQEVIRANEPIQPEEYTSNGDIHEFAFARKLKEAFNGGTINWLTTGNGIG
PTWAGFLPNANAAVFVDNHDTERNGETLTYKDGANYDLAQIFTLAWNYGSPSIHSGYSFS
NNDAGPALAGNGEVIDPVCGQNGWTCKHAQTGIENMVGFRTQTYGTAVVNKWDNGSSAIA
FGRGDKGYVAINRGSALTRTFQTSLPAGNYCNVIVGLPNSTGCSAGGVVTVDAAGTFTAT
VDQNSAFALHVGAKAGTQQPGPGAGDMKVYYSTSKGWSDYKIHYRVGTGAWTTAPGAGMT
AACAGWVSYTVPAGSTGATAAFNNGSGTWDNNNTSNYALSGAVSTVNGGVVGHTDPCTES
APAPADTAVVFYSTNKGWSAYNIHYRVGTGAWTTAPGSAMTAACTGWMTASIPLGGASGI
TAAFNNGAGTWDNNAGADYSVGSGYRQVKDGVVSTGNPCA

SEQ ID NO: 19: Amino acid sequence of the linker separating CBM 25(1) from CBM 25(2).
DPCEAQPAPGEDPDLTV

*FIG. 8E*

SEQUENCE LISTING

```
<160> NUMBER OF SEQ ID NOS: 19

<210> SEQ ID NO 1
<211> LENGTH: 440
<212> TYPE: DNA
<213> ORGANISM: Nesterenkonia xinjiangensis

<400> SEQUENCE: 1
cgtgcttgca cgggtggatt agtggcgaac gggtgagtat cacgtgagta acctgcccct     60
gactctggga taagcctggg aaactgggtc taataccgga tgcgaccagt ccccgcatgg    120
ggtgctggtg gaaagatttt atcggtcttg gatggactcg cggcctatca gctagacggt    180
ggggtagaag cccaccgtgg cgatgacggg tagccggcct gagagggtga ccggccacac    240
tgggactgag acacggccca gactcctacg ggaggcagca gtggggaata ttgcacaatg    300
ggcgcaagcc tgatgcagcg acgccgcgtg cgggatgacg gccttcgggt tgtaaaccgc    360
tttcagcagg gaagaagctt tattgtgacg gtacctgcag aagaagcgcc ggctaactac    420
gtgccagcag ccgcggtaat                                                 440

<210> SEQ ID NO 2
<211> LENGTH: 24
<212> TYPE: DNA
<213> ORGANISM: Artificial
<220> FEATURE:
<223> OTHER INFORMATION: synthetic primer

<400> SEQUENCE: 2
cataagatta gcggatccta cctg                                             24

<210> SEQ ID NO 3
<211> LENGTH: 25
<212> TYPE: DNA
<213> ORGANISM: Artificial
<220> FEATURE:
<223> OTHER INFORMATION: synthetic primer

<400> SEQUENCE: 3
cagcttgtcc agcagggttg tccac                                            25

<210> SEQ ID NO 4
<211> LENGTH: 24
<212> TYPE: DNA
<213> ORGANISM: Artificial
<220> FEATURE:
<223> OTHER INFORMATION: synthetic primer

<400> SEQUENCE: 4
gtgaggtctg cacatagccg taac                                             24

<210> SEQ ID NO 5
<211> LENGTH: 24
<212> TYPE: DNA
<213> ORGANISM: Artificial
<220> FEATURE:
<223> OTHER INFORMATION: synthetic primer

<400> SEQUENCE: 5
```
gtactgcaac gtctacaccg gctc                                                          24

<210> SEQ ID NO 6
<211> LENGTH: 23
<212> TYPE: DNA
<213> ORGANISM: Artificial
<220> FEATURE:
<223> OTHER INFORMATION: synthetic primer

<400> SEQUENCE: 6
ggaatgcgac ctgctcggac tcg                                                           23

<210> SEQ ID NO 7
<211> LENGTH: 2172
<212> TYPE: DNA
<213> ORGANISM: Nesterenkonia xinjiangensis

<400> SEQUENCE: 7
gtgcggacgg caggggctct cggactggcc ggtgccatgc tggcacccgc caccatgcct         60
gcggccaccg ccttcgacgg cgggcccccg gcctccgaca ggcggccgga tcacgccggc        120
gcccgcggcg cggagaacgc ctcgcagaac tccgcccacc acaccgaccg gctcccggag        180
ctccgcaccg cggcgcagag cgcggagggg acgaaggaca ccaccgccgt gatgttccag        240
tggacgtgga acagcatcgc ccgcgaatgc cgtgagacgc tcggcccggc cggttacggc        300
tatgtgcaga cctcaccggc ccaggagcac atccacggtg agccgtggtg gacccactat        360
cagccggtga gctaccagat cgaatctcgc ctgggtaccc gcgacgagtt cgcggacatg        420
gtctccacct gcaacgacgc cggcgtgaag gtcatcgccg acgtcgtcat caaccacatg        480
acgggacagg acgagggcgt gggttgggcc ggcagcgagt tcacccacac gaactatccc        540
ggcacctact ccccgacga cttccacaac cacggctgcg aggtggagga ctacaccgac        600
cgctggcaag tccaggaatg cgacctgctc ggactcgccg atctgaagac cagctccgac        660
tacgtccagt cgcggatcgg cgaacacctc gaggacctca tcgacctcgg cgtcgagggc        720
ttccgcatcg atgcggtcaa gcacatctcc gccgacgacc tcaccggcat cctggaccgt        780
gtggacctga ccgacatcta cgtggtctcc gaggtcatcc gcggcggcgg cgaacccatc        840
cagcccgagg agtaccagca cctgggcgac gtccacgaat tcacctgggg ccggaagctc        900
aaagaggcct tcgacggcgg cgacatccac tggctgctct ccggcgaggg catcggtgag        960
acctgggaag gcttcatcgc cgacgagcac gccggcacct tcgtggacaa ccacgacacc       1020
gaacgcaacg cgagaccct gagctacaag gacggggacg cctaccgcct ggcccaggcc       1080
ttcacgctgg cctggccgta cggcatgccc gcggtgcact ccggctactc gttcagcgac       1140
tacgacgccg gccccgtgca gcatgaggac ggtcggatcc gcgacgcggt ctgcggcgag       1200
gagaactgga cctgcatcca cgcccagacc gaggtggcca acatggtcgg gttccgcaac       1260
gccgtcgggg acgccccggt gaccgacacg tggaccaacg actcccacgc cctggccttc       1320
ggccgtggcg accagggctt cctggtggcc aaccgcggac gaacagtgt gcagcacacc       1380
tggcagacct ccttgccggc cggcgagtac tgcaacgtct acaccggctc cgccacgtcc       1440
gagggttgct ccggggaaac cgtgaccgtg gcggccgacg gcaccttcag cgcccacgtg       1500
ggcccggact ccgccgtggc tctgcacgtg ggcgccaccc cggccagcgg cgacggagac       1560
ggcgacggtg acggatcgac gccgccggag gagcgcgagc tgtccctgtt ctacgccacc       1620
gactgggaga ccccgcacgt ccactaccag gtgggcgacg gcgagtggac ggacctgccc       1680
ggcctggcca tgaccgaggc ctgcgaggga tggttccacg ccgagatcga cctcggcacg       1740

```
gcccggacca tcaccgcggc attcaacgac ggcggcgacg cctgggacaa caacgacggt    1800
gaggactaca cgatcggctc cggcgtcatc caggtctcgg acagccagct ggccgagggc    1860 gaccccctgcg aggcccaacc cgccccgggc gaggaccccg acctgaccgt gtactacgag    1920
accggctggg agaacccgcg cattcactac caggagggcg acggcggctg gacggacgtt    1980
ccgggtgtgg caatggccga ggcctgtgag ggctggttcc gggcggacat ccagctcgac    2040
gacgcggacg gcatcaccgc ggccttcaac gacggcgccg gcacctggga caacaacgac    2100
catcaggact acagcatcgc cgccggcgag cagcaagtgt caggaggcga ggtcactgca    2160 ggcaaccccct gt                                                        2172
```

<210> SEQ ID NO 8
<211> LENGTH: 2100
<212> TYPE: DNA
<213> ORGANISM: Nesterenkonia xinjiangensis

<400> SEQUENCE: 8

```
ttcgacggcg ggcccccggc ctccgacaag gcggccgatc acgccggcgc ccgcggcgcg     60
gagaacgcct cgcagaactc cgcccaccac accgaccggc tcccggagct ccgcaccgcg    120
gcgcagagcg cggaggggac gaaggacacc accgccgtga tgttccagtg acgtggaaac    180
agcatcgccc gcgaatgccg tgagacgctc ggcccggccg gttacggcta tgtgcagacc    240
tcaccggccc aggagcacat ccacggtgag ccgtggtgga cccactatca gccggtgagc    300
taccagatcg aatctcgcct gggtacccgc gacgagttcg cggacatggt ctccacctgc    360
aacgacgccg gcgtgaaggt catcgccgac gtcgtcatca accacatgac gggacaggac    420
gagggcgtgg gttgggccgg cagcgagttc acccacacga actatcccgg cacctactcc    480
cccgacgact tccacaacca cggctgcgag gtggaggact acaccgaccg ctggcaagtc    540
caggaatgcg acctgctcgg actcgccgat ctgaagacca gctccgacta cgtccagtcg    600
cggatcggcg aacacctcga ggacctcatc gacctcggcg tcgagggctt ccgcatcgat    660
gcggtcaagc acatctccgc cgacgacctc accggcatcc tggaccgtgt ggacctgacc    720
gacatctacg tggtctccga ggtcatccgc ggcggcggcc aacccatcca gcccgaggag    780
taccagcacc tggcgacgt ccacgaattc acctggggcc ggaagctcaa agaggccttc    840 gacggcggc acatccactg gctgctctcc ggcgagggca tcggtgagac ctgggaaggc    900
ttcatcgccg acgagcacgc cggcaccttc gtggacaacc acgacaccga acgcaacggc    960
gagaccctga gctacaagga cggggacgcc taccgcctgg cccaggcctt cacgctggcc    1020
tggccgtacg gcatgcccgc ggtgcactcc ggctactcgt tcagcgacta cgacgccggc    1080
cccgtgcagc atgaggacgg tcggatccgc gacgcggtct gcggcgagga gaactggacc    1140
tgcatccacg cccagaccga ggtggccaac atggtcgggt tccgcaacgc cgtcggggac    1200
gccccggtga ccgacacgtg gaccaacgac tcccacgccc tggccttcgg ccgtggcgac    1260
cagggcttcc tggtggccaa ccgcggaccg aacagtgtgc agcacacctg gcagacctcc    1320
ttgccggccg gcgagtactg caacgtctac accggctccg ccacgtccga gggttgctcc    1380
ggggaaaccg tgaccgtggc ggccgacggc accttcagcg cccacgtggg cccggactcc    1440
gccgtggctc tgcacgtggg cgccaccccg ccagcggcg acggagacgg cgacggtgac    1500
ggatcgacgc cgccggagga gcgcgagctg tccctgttct acgccaccga ctgggagacc    1560
ccgcacgtcc actaccaggt gggcgacggc gagtggacgg acctgcccgg cctggccatg    1620
```

-continued

```
accgaggcct gcgagggatg gttccacgcc gagatcgacc tcggcacggc ccggaccatc    1680
accgcggcat tcaacgacgg cggcgacgcc tgggacaaca cgacggtga ggactacacg     1740 atcggctccg gcgtcatcca ggtctcggac agccagctgg ccgagggcga ccctgcgag     1800 gcccaacccg ccccgggcga ggaccccgac ctgaccgtgt actacgagac cggctgggag    1860
aacccgcgca ttcactacca ggagggcgac ggcggctgga cggacgttcc gggtgtggca    1920
atggccgagg cctgtgaggg ctggttccgg gcggacatcc agctcgacga cgcggacggc    1980
atcaccgcgg ccttcaacga cggcgccggc acctgggaca caacgacca tcaggactac     2040 agcatcgccg ccggcgagca gcaagtgtca ggaggcgagg tcactgcagg caacccctgt    2100
```

<210> SEQ ID NO 9
<211> LENGTH: 724
<212> TYPE: PRT
<213> ORGANISM: Nesterenkonia xinjiangensis

<400> SEQUENCE: 9

```
Met Arg Thr Ala Gly Ala Leu Gly Leu Ala Gly Ala Met Leu Ala Pro
1               5                   10                  15

Ala Thr Met Pro Ala Ala Thr Ala Phe Asp Gly Gly Pro Pro Ala Ser
            20                  25                  30

Asp Lys Ala Ala Asp His Ala Gly Ala Arg Gly Ala Glu Asn Ala Ser
        35                  40                  45

Gln Asn Ser Ala His His Thr Asp Arg Leu Pro Glu Leu Arg Thr Ala
    50                  55                  60

Ala Gln Ser Ala Glu Gly Thr Lys Asp Thr Thr Ala Val Met Phe Gln
65                  70                  75                  80

Trp Thr Trp Asn Ser Ile Ala Arg Glu Cys Arg Glu Thr Leu Gly Pro
                85                  90                  95

Ala Gly Tyr Gly Tyr Val Gln Thr Ser Pro Ala Gln Glu His Ile His
            100                 105                 110

Gly Glu Pro Trp Trp Thr His Tyr Gln Pro Val Ser Tyr Gln Ile Glu
        115                 120                 125

Ser Arg Leu Gly Thr Arg Asp Glu Phe Ala Asp Met Val Ser Thr Cys
    130                 135                 140

Asn Asp Ala Gly Val Lys Val Ile Ala Asp Val Val Ile Asn His Met
145                 150                 155                 160

Thr Gly Gln Asp Glu Gly Val Gly Trp Ala Gly Ser Glu Phe Thr His
                165                 170                 175

Thr Asn Tyr Pro Gly Thr Tyr Ser Pro Asp Asp Phe His Asn His Gly
            180                 185                 190

Cys Glu Val Glu Asp Tyr Thr Asp Arg Trp Gln Val Gln Glu Cys Asp
        195                 200                 205

Leu Leu Gly Leu Ala Asp Leu Lys Thr Ser Ser Asp Tyr Val Gln Ser
    210                 215                 220

Arg Ile Gly Glu His Leu Glu Asp Leu Ile Asp Leu Gly Val Glu Gly
225                 230                 235                 240

Phe Arg Ile Asp Ala Val Lys His Ile Ser Ala Asp Asp Leu Thr Gly
                245                 250                 255

Ile Leu Asp Arg Val Asp Leu Thr Asp Ile Tyr Val Val Ser Glu Val
            260                 265                 270

Ile Arg Gly Gly Gly Glu Pro Ile Gln Pro Glu Glu Tyr Gln His Leu
        275                 280                 285

Gly Asp Val His Glu Phe Thr Trp Gly Arg Lys Leu Lys Glu Ala Phe
```

```
            290                 295                 300
Asp Gly Gly Asp Ile His Trp Leu Leu Ser Gly Glu Gly Ile Gly Glu
305                 310                 315                 320

Thr Trp Glu Gly Phe Ile Ala Asp Glu His Ala Gly Thr Phe Val Asp
                    325                 330                 335

Asn His Asp Thr Glu Arg Asn Gly Glu Thr Leu Ser Tyr Lys Asp Gly
                340                 345                 350

Asp Ala Tyr Arg Leu Ala Gln Ala Phe Thr Leu Ala Trp Pro Tyr Gly
                355                 360                 365

Met Pro Ala Val His Ser Gly Tyr Ser Phe Ser Asp Tyr Asp Ala Gly
370                 375                 380

Pro Val Gln His Glu Asp Gly Arg Ile Arg Asp Ala Val Cys Gly Glu
385                 390                 395                 400

Glu Asn Trp Thr Cys Ile His Ala Gln Thr Glu Val Ala Asn Met Val
                405                 410                 415

Gly Phe Arg Asn Ala Val Gly Asp Ala Pro Val Thr Asp Thr Trp Thr
                420                 425                 430

Asn Asp Ser His Ala Leu Ala Phe Gly Arg Gly Asp Gln Gly Phe Leu
                435                 440                 445

Val Ala Asn Arg Gly Pro Asn Ser Val Gln His Thr Trp Gln Thr Ser
450                 455                 460

Leu Pro Ala Gly Glu Tyr Cys Asn Val Tyr Thr Gly Ser Ala Thr Ser
465                 470                 475                 480

Glu Gly Cys Ser Gly Glu Thr Val Thr Val Ala Ala Asp Gly Thr Phe
                485                 490                 495

Ser Ala His Val Gly Pro Asp Ser Ala Val Ala Leu His Val Gly Ala
                500                 505                 510

Thr Pro Ala Ser Gly Asp Gly Asp Gly Asp Gly Ser Thr Pro
                515                 520                 525

Pro Glu Glu Arg Glu Leu Ser Leu Phe Tyr Ala Thr Asp Trp Glu Thr
530                 535                 540

Pro His Val His Tyr Gln Val Gly Asp Gly Glu Trp Thr Asp Leu Pro
545                 550                 555                 560

Gly Leu Ala Met Thr Glu Ala Cys Glu Gly Trp Phe His Ala Glu Ile
                565                 570                 575

Asp Leu Gly Thr Ala Arg Thr Ile Thr Ala Ala Phe Asn Asp Gly Gly
                580                 585                 590

Asp Ala Trp Asp Asn Asn Asp Gly Glu Asp Tyr Thr Ile Gly Ser Gly
                595                 600                 605

Val Ile Gln Val Ser Asp Ser Gln Leu Ala Glu Gly Asp Pro Cys Glu
610                 615                 620

Ala Gln Pro Ala Pro Gly Glu Asp Pro Asp Leu Thr Val Tyr Tyr Glu
625                 630                 635                 640

Thr Gly Trp Glu Asn Pro Arg Ile His Tyr Gln Glu Gly Asp Gly Gly
                645                 650                 655

Trp Thr Asp Val Pro Gly Val Ala Met Ala Glu Ala Cys Glu Gly Trp
                660                 665                 670

Phe Arg Ala Asp Ile Gln Leu Asp Asp Ala Asp Gly Ile Thr Ala Ala
                675                 680                 685

Phe Asn Asp Gly Ala Gly Thr Trp Asp Asn Asn Asp His Gln Asp Tyr
                690                 695                 700

Ser Ile Ala Ala Gly Glu Gln Gln Val Ser Gly Gly Glu Val Thr Ala
705                 710                 715                 720
```

Gly Asn Pro Cys

<210> SEQ ID NO 10
<211> LENGTH: 24
<212> TYPE: PRT
<213> ORGANISM: Nesterenkonia xinjiangensis

<400> SEQUENCE: 10

Met Arg Thr Ala Gly Ala Leu Gly Leu Ala Gly Ala Met Leu Ala Pro
1               5                   10                  15

Ala Thr Met Pro Ala Ala Thr Ala
            20

<210> SEQ ID NO 11
<211> LENGTH: 700
<212> TYPE: PRT
<213> ORGANISM: Nesterenkonia xinjiangensis

<400> SEQUENCE: 11

Phe Asp Gly Gly Pro Pro Ala Ser Asp Lys Ala Ala Asp His Ala Gly
1               5                   10                  15

Ala Arg Gly Ala Glu Asn Ala Ser Gln Asn Ser Ala His His Thr Asp
            20                  25                  30

Arg Leu Pro Glu Leu Arg Thr Ala Ala Gln Ser Ala Glu Gly Thr Lys
        35                  40                  45

Asp Thr Thr Ala Val Met Phe Gln Trp Thr Trp Asn Ser Ile Ala Arg
    50                  55                  60

Glu Cys Arg Glu Thr Leu Gly Pro Ala Gly Tyr Gly Tyr Val Gln Thr
65                  70                  75                  80

Ser Pro Ala Gln Glu His Ile His Gly Glu Pro Trp Trp Thr His Tyr
                85                  90                  95

Gln Pro Val Ser Tyr Gln Ile Glu Ser Arg Leu Gly Thr Arg Asp Glu
            100                 105                 110

Phe Ala Asp Met Val Ser Thr Cys Asn Asp Ala Gly Val Lys Val Ile
        115                 120                 125

Ala Asp Val Val Ile Asn His Met Thr Gly Gln Asp Glu Gly Val Gly
    130                 135                 140

Trp Ala Gly Ser Glu Phe Thr His Thr Asn Tyr Pro Gly Thr Tyr Ser
145                 150                 155                 160

Pro Asp Asp Phe His Asn His Gly Cys Glu Val Glu Asp Tyr Thr Asp
                165                 170                 175

Arg Trp Gln Val Gln Glu Cys Asp Leu Leu Gly Leu Ala Asp Leu Lys
            180                 185                 190

Thr Ser Ser Asp Tyr Val Gln Ser Arg Ile Ala Glu His Leu Glu Asp
        195                 200                 205

Leu Ile Asp Leu Gly Val Glu Gly Phe Arg Ile Asp Ala Val Lys His
    210                 215                 220

Ile Ser Ala Asp Asp Leu Thr Gly Ile Leu Asp Arg Val Asp Leu Thr
225                 230                 235                 240

Asp Ile Tyr Val Val Ser Glu Val Ile Arg Gly Gly Glu Pro Ile
                245                 250                 255

Gln Pro Glu Glu Tyr Gln His Leu Gly Asp Val His Glu Phe Thr Trp
            260                 265                 270

Gly Arg Lys Leu Lys Glu Ala Phe Asp Gly Gly Asp Ile His Trp Leu
        275                 280                 285

```
Leu Ser Gly Glu Gly Ile Gly Glu Thr Trp Glu Gly Phe Ile Ala Asp
    290                 295                 300

Glu His Ala Gly Thr Phe Val Asp Asn His Asp Thr Glu Arg Asn Gly
305                 310                 315                 320

Glu Thr Leu Ser Tyr Lys Asp Gly Asp Ala Tyr Arg Leu Ala Gln Ala
                325                 330                 335

Phe Thr Leu Ala Trp Pro Tyr Gly Met Pro Ala Val His Ser Gly Tyr
                340                 345                 350

Ser Phe Ser Asp Tyr Asp Ala Gly Pro Val Gln His Glu Asp Gly Arg
        355                 360                 365

Ile Arg Asp Ala Val Cys Gly Glu Asn Trp Thr Cys Ile His Ala
370                 375                 380

Gln Thr Glu Val Ala Asn Met Val Gly Phe Arg Asn Ala Val Gly Asp
385                 390                 395                 400

Ala Pro Val Thr Asp Thr Trp Thr Asn Asp Ser His Ala Leu Ala Phe
                405                 410                 415

Gly Arg Gly Asp Gln Gly Phe Leu Val Ala Asn Arg Gly Pro Asn Ser
            420                 425                 430

Val Gln His Thr Trp Gln Thr Ser Leu Pro Ala Gly Glu Tyr Cys Asn
                435                 440                 445

Val Tyr Thr Gly Ser Ala Thr Ser Glu Gly Cys Ser Gly Glu Thr Val
    450                 455                 460

Thr Val Ala Ala Asp Gly Thr Phe Ser Ala His Val Gly Pro Asp Ser
465                 470                 475                 480

Ala Val Ala Leu His Val Gly Ala Thr Leu Ala Ser Gly Asp Gly Asp
                485                 490                 495

Gly Asp Gly Asp Gly Ser Thr Pro Pro Glu Glu Arg Glu Leu Ser Leu
            500                 505                 510

Phe Tyr Ala Thr Asp Trp Glu Thr Pro His Val His Tyr Gln Val Gly
                515                 520                 525

Asp Gly Glu Trp Thr Asp Leu Pro Gly Leu Ala Met Thr Glu Ala Cys
        530                 535                 540

Glu Gly Trp Phe His Ala Glu Ile Asp Leu Gly Thr Ala Arg Thr Ile
545                 550                 555                 560

Thr Ala Ala Phe Asn Asp Gly Asp Ala Trp Asp Asn Asn Asp Gly
                565                 570                 575

Glu Asp Tyr Thr Ile Gly Ser Gly Val Ile Gln Val Ser Asp Ser Gln
            580                 585                 590

Leu Ala Glu Gly Asp Pro Cys Glu Ala Gln Pro Ala Pro Gly Glu Asp
        595                 600                 605

Pro Asp Leu Thr Val Tyr Tyr Glu Thr Gly Trp Glu Asn Pro Arg Ile
        610                 615                 620

His Tyr Gln Glu Gly Asp Gly Gly Trp Thr Asp Val Pro Gly Val Ala
625                 630                 635                 640

Met Ala Glu Ala Cys Glu Gly Trp Phe Arg Ala Asp Ile Gln Leu Asp
                645                 650                 655

Asp Ala Asp Gly Ile Thr Ala Ala Phe Asn Asp Gly Ala Gly Thr Trp
                660                 665                 670

Asp Asn Asn Asp His Gln Asp Tyr Ser Ile Ala Ala Gly Glu Gln Gln
            675                 680                 685

Val Ser Gly Gly Glu Val Thr Ala Gly Asn Pro Cys
    690                 695                 700
```

-continued

```
<210> SEQ ID NO 12
<211> LENGTH: 84
<212> TYPE: PRT
<213> ORGANISM: Artificial
<220> FEATURE:
<223> OTHER INFORMATION: synthetic carbohydrate binding module

<400> SEQUENCE: 12

Phe Tyr Ala Thr Asp Trp Glu Thr Pro His Val His Tyr Gln Val Gly
1               5                   10                  15

Asp Gly Glu Trp Thr Asp Leu Pro Gly Leu Ala Met Thr Glu Ala Cys
            20                  25                  30

Glu Gly Trp Phe His Ala Glu Ile Asp Leu Gly Thr Ala Arg Thr Ile
        35                  40                  45

Thr Ala Ala Phe Asn Asp Gly Gly Asp Ala Trp Asp Asn Asn Asp Gly
    50                  55                  60

Glu Asp Tyr Thr Ile Gly Ser Gly Val Ile Gln Val Ser Asp Ser Gln
65                  70                  75                  80

Leu Ala Glu Gly

<210> SEQ ID NO 13
<211> LENGTH: 84
<212> TYPE: PRT
<213> ORGANISM: Artificial
<220> FEATURE:
<223> OTHER INFORMATION: synthetic carbohydrate binding module

<400> SEQUENCE: 13

Tyr Tyr Glu Thr Gly Trp Glu Asn Pro Arg Ile His Tyr Gln Glu Gly
1               5                   10                  15

Asp Gly Gly Trp Thr Asp Val Pro Gly Val Ala Met Ala Glu Ala Cys
            20                  25                  30

Glu Gly Trp Phe Arg Ala Asp Ile Gln Leu Asp Asp Ala Asp Gly Ile
        35                  40                  45

Thr Ala Ala Phe Asn Asp Gly Ala Gly Thr Trp Asp Asn Asn Asp His
    50                  55                  60

Gln Asp Tyr Ser Ile Ala Ala Gly Glu Gln Gln Val Ser Gly Gly Glu
65                  70                  75                  80

Val Thr Ala Gly

<210> SEQ ID NO 14
<211> LENGTH: 47
<212> TYPE: DNA
<213> ORGANISM: Artificial
<220> FEATURE:
<223> OTHER INFORMATION: synthetic primer

<400> SEQUENCE: 14
ctcattctgc agcttcagca gctgcggagg ggacgaagga caccacc          47

<210> SEQ ID NO 15
<211> LENGTH: 41
<212> TYPE: DNA
<213> ORGANISM: Artificial
<220> FEATURE:
<223> OTHER INFORMATION: synthetic primer

<400> SEQUENCE: 15
gtcctctgtt aactcaacag gggttgccag cagtgacctc g                41

<210> SEQ ID NO 16
```

-continued

```
<211> LENGTH: 22
<212> TYPE: DNA
<213> ORGANISM: Artificial
<220> FEATURE:
<223> OTHER INFORMATION: synthetic primer

<400> SEQUENCE: 16
tacatatgag ttatgcagtt tg                                              22

<210> SEQ ID NO 17
<211> LENGTH: 22
<212> TYPE: DNA
<213> ORGANISM: Artificial
<220> FEATURE:
<223> OTHER INFORMATION: synthetic primer

<400> SEQUENCE: 17
gttatgagtt agttcaaatt cg                                              22

<210> SEQ ID NO 18
<211> LENGTH: 700
<212> TYPE: PRT
<213> ORGANISM: Bacillus sp. 195

<400> SEQUENCE: 18
```

Met Pro Ala Leu Tyr Gln Gly Val Ile Ala Asp Val Arg Ala Lys Arg
1               5                   10                  15

Lys Arg Leu Gln Val Leu Ala Lys Met Val Leu Ile Ala Leu Leu Gly
            20                  25                  30

Thr Leu Leu Ser Ala Thr Ala Phe Ala Ala Pro Ala Ser Ala Ala Ala
        35                  40                  45

Pro Gly Pro Lys Asp Ala Thr Ala Val Met Phe Ser Trp Thr Trp Asn
    50                  55                  60

Ala Ile Ala Arg Glu Cys Thr Glu Asn Leu Gly Pro Ala Gly Tyr Gly
65                  70                  75                  80

Tyr Val Gln Thr Ser Pro Pro Gln Glu His Ile Gln Gly Ala Ala Trp
                85                  90                  95

Trp Thr His Tyr Gln Pro Val Ser Tyr Lys Ile Glu Ser Arg Phe Gly
            100                 105                 110

Thr Arg Ala Glu Phe Lys Ala Met Val Asp Thr Cys His Ala Ala Gly
        115                 120                 125

Val Lys Val Ile Ala Asp Ala Val Ile Asn His Met Thr Gly Gln Ser
    130                 135                 140

Ala Gly Gly Thr Gly Trp Ala Gly Ser Thr Phe Gln His Tyr Asp Tyr
145                 150                 155                 160

Pro Gly Ile Tyr Gln Ser Gln Asp Phe His Ser Cys Arg Arg Asn Ile
                165                 170                 175

Ala Asn Tyr Gln Asp Arg Trp Glu Val Gln Glu Cys Asn Leu Val Asn
            180                 185                 190

Leu Ala Asp Leu Asn Thr Ser Ser Tyr Val Gln Gly Lys Ile Ala
        195                 200                 205

Ala Tyr Leu Asn Asp Leu Val Ser Leu Gly Val Asp Gly Leu Arg Ile
    210                 215                 220

Asp Ala Val Lys His Ile Ala Ala Ser Asp Met Gln Gly Ile Leu Ser
225                 230                 235                 240

Lys Val Asn Asp Arg Ala Arg Leu Tyr Ile Val Gln Glu Val Ile Arg
                245                 250                 255

Ala Asn Glu Pro Ile Gln Pro Glu Glu Tyr Thr Ser Asn Gly Asp Ile

```
                260                 265                 270
His Glu Phe Ala Phe Ala Arg Lys Leu Lys Glu Ala Phe Asn Gly Gly
                275                 280                 285

Thr Ile Asn Trp Leu Thr Thr Gly Asn Gly Ile Gly Pro Thr Trp Ala
            290                 295                 300

Gly Phe Leu Pro Asn Ala Asn Ala Ala Val Phe Val Asp Asn His Asp
305                 310                 315                 320

Thr Glu Arg Asn Gly Glu Thr Leu Thr Tyr Lys Asp Gly Ala Asn Tyr
                325                 330                 335

Asp Leu Ala Gln Ile Phe Thr Leu Ala Trp Asn Tyr Gly Ser Pro Ser
                340                 345                 350

Ile His Ser Gly Tyr Ser Phe Ser Asn Asn Asp Ala Gly Pro Ala Leu
            355                 360                 365

Ala Gly Asn Gly Glu Val Ile Asp Pro Val Cys Gly Gln Asn Gly Trp
370                 375                 380

Thr Cys Lys His Ala Gln Thr Gly Ile Glu Asn Met Val Gly Phe Arg
385                 390                 395                 400

Thr Gln Thr Tyr Gly Thr Ala Val Val Asn Lys Trp Asp Asn Gly Ser
                405                 410                 415

Ser Ala Ile Ala Phe Gly Arg Gly Asp Lys Gly Tyr Val Ala Ile Asn
                420                 425                 430

Arg Gly Ser Ala Leu Thr Arg Thr Phe Gln Thr Ser Leu Pro Ala Gly
            435                 440                 445

Asn Tyr Cys Asn Val Ile Val Gly Leu Pro Asn Ser Thr Gly Cys Ser
            450                 455                 460

Ala Gly Gly Val Val Thr Val Asp Ala Ala Gly Thr Phe Thr Ala Thr
465                 470                 475                 480

Val Asp Gln Asn Ser Ala Phe Ala Leu His Val Gly Ala Lys Ala Gly
                485                 490                 495

Thr Gln Gln Pro Gly Pro Gly Ala Gly Asp Met Lys Val Tyr Tyr Ser
                500                 505                 510

Thr Ser Lys Gly Trp Ser Asp Tyr Lys Ile His Tyr Arg Val Gly Thr
            515                 520                 525

Gly Ala Trp Thr Thr Ala Pro Gly Ala Gly Met Thr Ala Ala Cys Ala
            530                 535                 540

Gly Trp Val Ser Tyr Thr Val Pro Ala Gly Ser Thr Gly Ala Thr Ala
545                 550                 555                 560

Ala Phe Asn Asn Gly Ser Gly Thr Trp Asp Asn Asn Thr Ser Asn
                565                 570                 575

Tyr Ala Leu Ser Gly Ala Val Ser Thr Val Asn Gly Val Val Gly
            580                 585                 590

His Thr Asp Pro Cys Thr Glu Ser Ala Pro Ala Pro Asp Thr Ala
            595                 600                 605

Val Val Phe Tyr Ser Thr Asn Lys Gly Trp Ser Ala Tyr Asn Ile His
            610                 615                 620

Tyr Arg Val Gly Thr Gly Ala Trp Thr Thr Ala Pro Gly Ser Ala Met
625                 630                 635                 640

Thr Ala Ala Cys Thr Gly Trp Met Thr Ala Ser Ile Pro Leu Gly Gly
                645                 650                 655

Ala Ser Gly Ile Thr Ala Ala Phe Asn Asn Gly Ala Gly Thr Trp Asp
            660                 665                 670

Asn Asn Ala Gly Ala Asp Tyr Ser Val Gly Ser Gly Tyr Arg Gln Val
            675                 680                 685
```

```
Lys Asp Gly Val Val Ser Thr Gly Asn Pro Cys Ala
    690             695             700

<210> SEQ ID NO 19
<211> LENGTH: 17
<212> TYPE: PRT
<213> ORGANISM: Artificial
<220> FEATURE:
<223> OTHER INFORMATION: synthetic linker

<400> SEQUENCE: 19

Asp Pro Cys Glu Ala Gln Pro Ala Pro Gly Glu Asp Pro Asp Leu Thr
1               5                   10                  15

Val
```

AMYLASE FROM NESTERENKONIA AND METHODS OF USE, THEREOF

PRIORITY

The present application is a national phase filing under 35 USC §371 of International Application No. PCT/US2011/021884, filed on Jan. 20, 2011, which claims the benefit of U.S. Provisional Application Ser. No. 61/305,674, filed on Feb. 18, 2010, each of which are hereby incorporated by reference in their entirety.

TECHNICAL FIELD

Disclosed are compositions and methods relating to an amylase enzyme obtained from *Nesterenkonia* spp.

BACKGROUND

Starch consists of a mixture of amylose (15-30% w/w) and amylopectin (70-85% w/w). Amylose consists of linear chains of α-1,4-linked glucose units having a molecular weight (MW) from about 60,000 to about 800,000. Amylopectin is a branched polymer containing α-1,6 branch points every 24-30 glucose units; its MW may be as high as 100 million.

Sugars from starch, in the form of concentrated dextrose syrups, are currently produced by an enzyme catalyzed process involving: (1) liquefaction (or viscosity reduction) of solid starch with an α-amylase into dextrins having an average degree of polymerization of about 7-10, and (2) saccharification of the resulting liquefied starch (i.e. starch hydrolysate) with amyloglucosidase (also called glucoamylase or GA). The resulting syrup has a high glucose content. Much of the glucose syrup that is commercially produced is subsequently enzymatically isomerized to a dextrose/fructose mixture known as isosyrup.

α-amylases (EC 3.2.1.1) hydrolyze starch, glycogen, and related polysaccharides by cleaving internal α-1,4-glucosidic bonds at random. For a number of years, α-amylase enzymes have been used for a variety of different purposes, including starch liquefaction, textile desizing, starch modification in the paper and pulp industry, and for brewing. These enzymes can also be used to remove starchy stains during dishwashing and laundry washing. Laundry and dish soils vary greatly in composition and, therefore, in their ability to be effectively and efficiently removed.

*Nesterenkonia* spp. are Gram-positive bacteria classified as members of the Family Micrococcceae, Suborder Micrococcineae, Order Actinomycetales, Class Actinobacteria. *Nesterenkonia xinjianensis*, first described in 2004, was isolated from hypersaline soil samples from Xinjiang Province, China (Wen-Jun Li et al. (2004) *Int. J. Syst. Evol. Microbiol.* 54:837-41). *N. xinjiangensis* is not recognized as being an amylase-producing bacterium. In fact, the species description of the Type Strain indicates that the organism produces a negative reaction for starch hydrolysis, suggesting that amylases are not produced, or not secreted.

SUMMARY

The present compositions and methods relate to an alpha (α)-amylase from *Nesterenkonia* and related α-amylases, which are herein collectively referred to as AmyNEST.

In one aspect, an isolated AmyNEST polypeptide is provided. In some embodiments, the AmyNEST polypeptide is expressed in a heterologous organism. In particular embodiments, the AmyNEST polypeptide is expressed as a secreted polypeptide in a heterologous organism. In some embodiments, the AmyNEST polypeptide has at least 57%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, or even at least 99% amino acid sequence identity with SEQ ID NO: 11.

In some embodiments, the AmyNEST polypeptide has at least 57%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, or even at least 99% overall amino acid sequence identity with SEQ ID NO: 11, while including the amino acid sequence of carbohydrate binding module (CBM) 25(1) and/or CBM 25(2). In some embodiments, the AmyNEST polypeptide has at least 57%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, or even at least 99% overall amino acid sequence identity with SEQ ID NO: 11, while including an amino acid sequence that has at least 80%, at least 85%, at least 90%, at least 91%, at least 92%, at least 93%, at least 94%, at least 95%, at least 96%, at least 97%, at least 98%, or even at least 99% sequence identity with CBM 25(1) and/or CBM 25(2). In particular embodiments, the AmyNEST polypeptide includes an amino acid sequence that has at least 80%, at least 85%, at least 90%, at least 91%, at least 92%, at least 93%, at least 94%, at least 95%, at least 96%, at least 97%, at least 98%, or even at least 99% sequence identity with CBM 25(1) and an amino acid sequence that has at least 80%, at least 85%, at least 90%, at least 91%, at least 92%, at least 93%, at least 94%, at least 95%, at least 96%, at least 97%, at least 98%, or even at least 99% sequence identity with CBM 25(2). In some embodiments, the amino acid sequences relating to CBM 25(1) and CBM 25(2) in the AmyNEST polypeptide are separated by a linker.

In some embodiments, an AmyNEST polypeptide comprises an amino acid sequence having at least 60% amino acid sequence identity to the amino acid sequence of SEQ ID NO: 11 is provided. In particular embodiments, the polypeptide has at least 70% amino acid sequence identity to the amino acid sequence of SEQ ID NO: 11. In particular embodiments, the polypeptide has at least 80% amino acid sequence identity to the amino acid sequence of SEQ ID NO: 11. In particular embodiments, the polypeptide has at least 90% amino acid sequence identity to the amino acid sequence of SEQ ID NO: 11. In particular embodiments, the polypeptide has at least 95% amino acid sequence identity to the amino acid sequence of SEQ ID NO: 11. In some embodiments, the polypeptide comprises the amino acid sequence of carbohydrate binding module (CBM) 25(1) (SEQ ID NO: 12) and/or the amino acid sequence of CBM 25(2) (SEQ ID NO: 13). In particular embodiments, the polypeptide comprises the amino acid sequence of CBM 25(1) and the amino acid sequence of CBM 25(2) separated by a linker having the amino acid sequence of SEQ ID NO: 19. In some embodiments, the polypeptide has alpha-amylase activity, which can be determined, for example, by the assays described, herein.

In another aspect, a composition comprising an AmyNEST polypeptides is provided. In some embodiments, the composition is a cleaning composition. In some embodiments, the composition is effective for removing starchy stains from laundry, dishes, or textiles.

In another aspect, a method for removing a starchy stain from a surface is provided, comprising incubating the surface in the presence of a aqueous composition comprising an effective amount of an AmyNEST polypeptide, allowing the polypeptide to hydrolyse starch components present in the starchy stain to produce smaller starch-derived molecules that dissolve in the aqueous composition, thereby removing the starchy stain from the surface.

In some embodiments, the surface is a textile surface. In some embodiments, the surface is on dishes. In some embodiments, the surface is a soiled hard surface.

In another aspect, a method for expressing a polypeptide having amylase activity is provided, comprising:

constructing an expression vector comprising a polynucleotide encoding a signal sequence linked to a polynucleotide encoding an AmyNEST polypeptide;

introducing the expression vector into a host cell, expressing the polypeptides, recovering the polypeptide expressed.

In some embodiments, the AmyNEST polypeptide is introduced into a heterologous host cell. In some embodiments, the AmyNEST polypeptide is expressed as a secreted polypeptide.

In a further aspect, a vector comprising a polynucleotide sequence encoding an AmyNEST polypeptide is provided. The AmyNEST polypeptide-coding sequence may be operably linked to a promoter or to other control elements. In yet a further aspect, a host cell comprising a polynucleotide encoding an AmyNEST polypeptide, or vector comprising such a polynucleotide, is provided. The isolated host cell can be a prokaryote or eukaryote. The isolated host cell can be a bacterium (e.g., *B. subtilis, B. licheniformis, B. lentus, B. brevis, Geobacillus* (formerly *Bacillus*) *stearothermophilus, B. alkalophilus, B. amyloliquefaciens, B. coagulans, B. circulans, B. lautus, B. thuringiensis, Streptomyces lividans, S. murinus,* or *Escherichia coli*).

Another aspect contemplates a detergent additive comprising an AmyNEST polypeptide, wherein the detergent additive is optionally in the form of a non-dusting granulate, microgranulate, stabilized liquid, gel, or protected enzyme. The polypeptide in the detergent additive can be a truncated polypeptide as described above. The detergent additive can contain about 0.02 mg to about 200 mg of polypeptide per gram of the detergent additive. The detergent additive can further comprise an enzyme selected from the group consisting of a protease, a lipase, a peroxidase, an oxidase, an amylolytic enzyme, a cellulase, a polyesterase, and any combination thereof.

Another aspect contemplates a detergent composition comprising any of the described detergent additives. A detergent composition can optionally comprise one or more of: a surfactant, a bleaching system or bleach, a detergent builder, a polymer, a stabilizing agent, a fabric conditioner, a foam booster, a suds suppressor, an anti-corrosion agent, a dye, a perfume, a soil suspending agent, a tarnish inhibitor, an optical brightener, or a bacteriocide. A detergent composition can comprise or further comprise an additional enzyme, wherein the enzyme is a protease, a lipase, a peroxidase, an oxidase, an amylolytic enzyme, a cellulase, a polyesterase, or any combination thereof. In other embodiments, the composition is a detergent additive.

Another aspect contemplates a manual or automatic dishwashing detergent composition comprising an AmyNEST polypeptide.

Yet a further aspect contemplates a method of washing dishes comprising applying a manual or automatic dishwashing detergent described herein to a dish or dishes in need thereof. The method of washing the dishes contemplates adding the dishwashing detergent in an amount such that the wash liquor contains a polypeptide described herein in the amount of about 0.01 ppm to about 4 ppm.

Another aspect contemplates a laundry detergent composition comprising a detergent additive described herein. Yet a further aspect contemplates a method of cleaning a textile comprising washing a soiled textile in solution with a detergent composition described herein. The method further contemplates having the polypeptide described herein in an amount in the solution of about 0.01 to about 2 ppm in the solution.

These and other aspects and embodiments of the compositions and methods will be apparent from the present description and drawings.

BRIEF DESCRIPTION OF THE DRAWINGS

FIG. 8 lists the sequences referred to in the text.

BRIEF DESCRIPTION OF THE SEQUENCES

Figure 1:
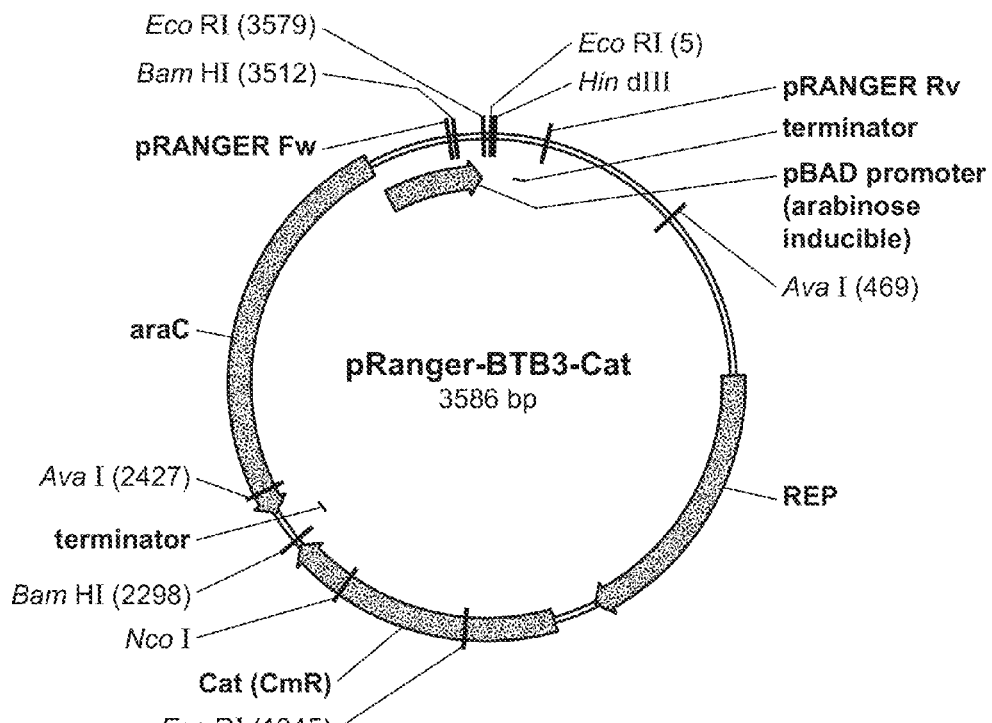
FIG. 1 is a plasmid map of vector pRANGER-BTB3-Cat.

SEQ ID NO: 1 is a partial nucleotide sequence of the *Nesterenkonia* xinjiangensis B4.2S6 16S rRNA gene.

SEQ ID NO: 2 is the nucleotide sequence of primer pRANGER-FW.

SEQ ID NO: 3 is the nucleotide sequence of primer pRANGER-RV.

SEQ ID NO: 4 is the nucleotide sequence of primer Nest-Insert3-RV.

SEQ ID NO: 5 is the nucleotide sequence of primer Nest-Insert3-FW.

SEQ ID NO: 6 is the nucleotide sequence of primer Nest-add-Fw.

SEQ ID NO: 7 is the nucleotide sequence of the *N. xinjiangensis* B4.2S6 α-amylase gene.

SEQ ID NO: 8 is the nucleotide sequence encoding the *N. xinjiangensis* B4.2S6 α-amylase mature protein.

SEQ ID NO: 9 is the amino acid sequence of the *N. xinjiangensis* B4.2S6 α-amylase precursor protein, including the 24-amino acid signal sequence.

SEQ ID NO: 10 is the amino acid sequence of the *N. xinjiangensis* B4.2S6 α-amylase signal peptide:

SEQ ID NO: 11 is the amino acid sequence of the *N. xinjiangensis* B4.2S6 α-amylase mature protein.

SEQ ID NO: 12 is the amino acid sequence of carbohydrate binding module CBM 25(1).

SEQ ID NO: 13 is the amino acid sequence of carbohydrate binding module CBM 25(2).

SEQ ID NO: 14 is the nucleotide sequence of primer pHPLT-AmyNest-Fw.

SEQ ID NO: 15 is the nucleotide sequence of primer pHPLT-AmyNest-Rv.

SEQ ID NO: 16 is the nucleotide sequence of primer pHPLT-F1.

SEQ ID NO: 17 is the nucleotide sequence of primer pHPLT-R1.

SEQ ID NO: 18 is the amino acid sequence of the immature form of *Bacillus* sp. 195 α-amylase.

SEQ ID NO: 19 is the amino acid sequence of the linker separating CBM 25(1) from CBM 25(2).

DETAILED DESCRIPTION

Described are compositions and methods relating to an α-amylase isolated from *Nesterenkonia*, and to variants and homologs, thereof. These polypeptides are collectively referred to as AmyNEST polypeptides.

Various compositions and methods that involve AmyNEST polypeptides, or polynucleotides encoding these polypeptides, are to be described.

1. Definitions and Acronyms

In accordance with this detailed description, the following abbreviations and definitions apply. Note that the singular forms "a," "an," and "the" include plural referents unless the context clearly dictates otherwise. Thus, for example, reference to an "enzyme" includes a plurality of such enzymes, and reference to the "dosage" includes reference to one or more dosages and equivalents thereof known to those skilled in the art, and so forth.

Unless defined otherwise, all technical and scientific terms used herein have the same meaning as commonly understood by one of ordinary skill in the art. The following abbreviations and/or terms are defined for clarity:

1.1 Abbreviations/Acronyms

The following abbreviations/acronyms have the following meanings unless otherwise specified:
AE alcohol ethoxylate
AEO alcohol ethoxylate
AEOS alcohol ethoxysulfate
AES alcohol ethoxysulfate
AOS α-olefinsulfonate
AS alkyl sulfate
CBD 25 carbohydrate binding domain protein family 25
cDNA complementary DNA
CMC carboxymethylcellulose
DNA deoxyribonucleic acid
DTMPA diethylenetriaminepentaacetic acid
EC enzyme commission
EDTA ethylenediaminetetraacetic acid
EMPA Eidgenössische Materialprüfungs- and Forschungs Anstalt (Swiss Federal Laboratories for Materials Testing and Research)
EO ethylene oxide (polymer fragment)
F&HC fabric & household care
GA glucoamylase
IPTG isopropyl β-D-thiogalactoside
kDa kiloDalton
LAS linear alkylbenzenesulfonate
LAT pertaining to *B. licheniformis* amylase
MW molecular weight
MWU modified Wohlgemuth unit; $1.6 \times 10^{-5}$ mg/MWU=unit of activity
NOBS nonanoyloxybenzenesulfonate
NTA nitriloacetic acid
OxAm Purastar HPAM 5000L (Genencor International, Inc.)
PEG polyethyleneglycol
pI isoelectric point
PVA poly(vinyl alcohol)
PVP poly(vinylpyrrolidone)
RNA ribonucleic acid
SAS alkanesulfonate
SDS-PAGE sodium dodecyl sulfate polyacrylamide gel electrophoresis
sp. species
TAED tetraacetylethylenediamine
w/v weight/volume
w/w weight/weight
v/v volume/volume
wt % weight percent
° C. degrees Centigrade
$H_2O$ water
$dH_2O$ or DI deionized water
$dIH_2O$ deionized water, Milli-Q filtration
g or gm gram
μg microgram
mg milligram
kg kilogram
μL and μl microliter
mL and ml milliliter
mm millimeter
μm micrometer
M molar
mM millimolar
μM micromolar
U unit
sec and ' second
min and " minute
hr hour
DO dissolved oxygen
Genencor Danisco US Inc, Genencor Division, Palo Alto, Calif.
Ncm Newton centimeter
ETOH ethanol
eq. equivalent
N normal
ds or DS dry solids content 1.2 Definitions The terms "amylase" or "amylolytic enzyme" refer to an enzyme that is, among other things, capable of catalyzing the degradation of starch. Amylases are hydrolases that cleave the α-D-(1→4) O-glycosidic linkages in starch. Generally, α-amylases (EC 3.2.1.1; α-D-(1→4)-glucan glucanohydrolase) are defined as endo-acting enzymes cleaving α-D-(1→4) O-glycosidic linkages within the starch molecule in a random fashion. In contrast, the exo-acting amylolytic enzymes, such as β-amylases (EC 3.2.1.2; α-D-(1→4)-glucan maltohydrolase) and some product-specific amylases like maltogenic α-amylase (EC 3.2.1.133) cleave the starch molecule from the non-reducing end of the substrate. β-Amylases, α-glucosidases (EC 3.2.1.20; α-D-glucoside glucohydrolase), glucoamylase (EC 3.2.1.3; α-D-(1→4)-glucan glucohydrolase), and product-specific amylases can produce malto-oligosaccharides of a specific length from starch.

As used herein the term "starch" refers to any material comprised of the complex polysaccharide carbohydrates of plants, comprised of amylose and amylopectin with the formula $(C_6H_{10}O_5)_x$, wherein X can be any number. The term includes plant-based materials such as grains, grasses, tubers and roots, and more specifically materials obtained from wheat, barley, corn, rye, rice, sorghum, brans, cassava, millet, potato, sweet potato, and tapioca.

The terms, "wild-type," "parental," or "reference," with respect to a polypeptide, refer to a naturally-occurring polypeptide that does not include a man-made substitution, insertion, or deletion at one or more amino acid positions. Similarly, the terms "wild-type," "parental," or "reference," with respect to a polynucleotide, refer to a naturally-occurring polynucleotide that does not include a man-made nucleoside change. However, note that a polynucleotide encoding a wild-type, parental, or reference polypeptide is not limited to a naturally-occurring polynucleotide, and encompasses any polynucleotide encoding the wild-type, parental, or reference polypeptide.

The term "variant," with respect to a polypeptide, refers to a polypeptide that differs from a specified wild-type, parental, or reference polypeptide in that it includes a man-made substitution, insertion, or deletion at one or more amino acid positions. Similarly, a the term "variant," with respect to a polynucleotide, refers to a polynucleotide that differs in nucleotide sequence from a specified wild-type, parental, or reference polynucleotide. The identity of the wild-type, parental, or reference polypeptide or polynucleotide will be apparent from context.

The term "recombinant," when used in reference to a subject cell, nucleic acid, protein or vector, indicates that the subject has been modified by the introduction of a heterologous nucleic acid or protein or the alteration of a native nucleic acid or protein, or that the cell is derived from a cell so modified. Thus, for example, recombinant cells express genes that are not found within the native (non-recombinant) form of the cell, or express native genes at different levels or under different conditions than found in nature.

The terms "recovered," "isolated," and "separated," refer to a compound, protein (polypeptides), cell, nucleic acid, amino acid, or other specified material or component that is removed from at least one other material or component with which it is naturally associated as found in nature.

As used herein, the term "purified" refers to material (e.g., an isolated polypeptide or polynucleotide) that is in a relatively pure state, e.g., at least about 90% pure, at least about 95% pure, at least about 98% pure, or even at least about 99% pure.

The terms "thermostable" and "thermostability," with reference to an enzyme, refer to the ability of the enzyme to retain activity after exposure to an elevated temperature. The thermostability of an enzyme, such as an amylase enzyme, is measured by its half-life ($t_{1/2}$) given in minutes, hours, or days, during which half the enzyme activity is lost under defined conditions. The half-life may be calculated by measuring residual α-amylase activity following exposure to (i.e., challenge by) an elevated temperature.

A "pH range," with reference to an enzyme, refers to the range of pH values under which the enzyme exhibits catalytic activity.

As used herein, the terms "pH stable" and "pH stability," with reference to an enzyme, relate to the ability of the enzyme to retain activity over a wide range of pH values for a predetermined period of time (e.g., 15 min, 30 min, 1 hour).

As used herein, the term "amino acid sequence" is synonymous with the terms "polypeptide," "protein," and "peptide," and are used interchangeably. Where such amino acid sequences exhibit activity, they may be referred to as an "enzyme." The conventional one-letter or three-letter codes for amino acid residues are used, with amino acid sequences being presented in the standard amino-to-carboxy terminal orientation (i.e., N→C).

The term "nucleic acid" encompasses DNA, RNA, heteroduplexes, and synthetic molecules capable of encoding a polypeptide. Nucleic acids may be single stranded or double stranded, and may be chemical modifications. The terms "nucleic acid" and "polynucleotide" are used interchangeably. Because the genetic code is degenerate, more than one codon may be used to encode a particular amino acid, and the present compositions and methods encompass nucleotide sequences which encode a particular amino acid sequence. Unless otherwise indicated, nucleic acid sequences are presented in a 5'-to-3' orientation.

By "homologue" shall mean an entity having a specified degree of identity with the subject amino acid sequences and the subject nucleotide sequences. A homologous sequence is taken to include an amino acid sequence that is at least 57%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, or even at least 99% identical to the subject sequence, using conventional sequence alignment tools (e.g., Clustal, BLAST, and the like). Typically, homologues will include the same active site residues as the subject amino acid sequence, unless otherwise specified.

As used herein, "hybridization" refers to the process by which one strand of nucleic acid base pairs with a complementary strand, as occurs during blot hybridization techniques and PCR techniques. Stringent hybridization conditions are exemplified by the following: 50° C. and 0.2×SSC (1×SSC=0.15 M NaCl, 0.015 M Na₃ citrate, pH 7.0). Highly stringent conditions are exemplified by the following: 65° C. and 0.1×SSC (1×SSC=0.15 M NaCl, 0.015 M Na₃ citrate, pH 7.0)].

As used herein, a "synthetic" molecule is produced by in vitro chemical or enzymatic synthesis rather than by an organism.

As used herein, the terms "transformed," "stably transformed," and "transgenic," used with reference to a cell means that the cell contains a non-native (e.g., heterologous) nucleic acid sequence integrated into its genome or carried as an episome that is maintained through multiple generations.

The term "introduced" in the context of inserting a nucleic acid sequence into a cell, means "transfection", "transformation" or "transduction," as known in the art.

A "host strain" or "host cell" is an organism into which an expression vector, phage, virus, or other DNA construct, including a polynucleotide encoding a polypeptide of interest (e.g., an AmyNEST polypeptide) has been introduced. Exemplary host strains are bacterial cells. The term "host cell" includes protoplasts created from cells, such as those of a *Bacillus* sp.

The term "heterologous" with reference to a polynucleotide or protein refers to a polynucleotide or protein that does not naturally occur in a host cell.

The term "endogenous" with reference to a polynucleotide or protein refers to a polynucleotide or protein that occurs naturally in the host cell.

As used herein, the term "expression" refers to the process by which a polypeptide is produced based on a nucleic acid sequence. The process includes both transcription and translation.

A "selective marker" or "selectable marker" refers to a gene capable of being expressed in a host to facilitate selection of host cells carrying the gene. Examples of selectable markers include but are not limited to antimicrobials (e.g., hygromycin, bleomycin, or chloramphenicol) and/or genes that confer a metabolic advantage, such as a nutritional advantage on the host cell.

A "vector" refers to a polynucleotide sequence designed to introduce nucleic acids into one or more cell types. Vectors include cloning vectors, expression vectors, shuttle vectors, plasmids, phage particles, cassettes and the like.

An "expression vector" refers to a DNA construct comprising a DNA sequence encoding a polypeptide of interest, which coding sequence is operably linked to a suitable control sequence capable of effecting expression of the DNA in a suitable host. Such control sequences may include a promoter to effect transcription, an optional operator sequence to control transcription, a sequence encoding suitable ribosome binding sites on the mRNA, enhancers and sequences that control termination of transcription and translation.

The term "operably linked" means that specified components are in a relationship (including but not limited to juxtaposition) permitting them to function in an intended manner. For example, a regulatory sequence is operably linked to a coding sequence such that expression of the coding sequence is under control of the regulatory sequences.

A "signal sequence" is a sequence of amino acids attached to the N-terminal portion of a protein, which facilitates the secretion of the protein outside the cell. The mature form of an extracellular protein lacks the signal sequence, which is cleaved off during the secretion process.

As used herein, "biologically active" refer to a sequence having a specified biological activity, such an enzymatic activity.

"Water hardness" is a measure of the minerals (e.g., calcium and magnesium) present in water.

As used herein, "a cultured cell material comprising an AmyNEST amylase (or AmyNEST polypeptide)," or similar language, refers to a cell lysate or supernatant that includes an AmyNEST polypeptide as a component. The cell material is preferably from a heterologous host that is grown in culture for the purpose of producing the AmyNEST polypeptide.

All reference cited, herein, are hereby incorporated by reference in their entirety.

2. AmyNEST Amylase Nucleic Acids and Polypeptides

One aspect of the present compositions and methods is an α-amylase polypeptide obtained from a species of the genus *Nesterenkonia*, or to structurally-related polypeptides, which are collectively referred to as AmyNEST amylases or AmyNEST polypeptides. An exemplary AmyNEST polypeptide is obtained from *N. xinjiangensis* strain B4.2S6, and has the amino acid sequence of SEQ ID NO: 11. The genus *Nesterenkonia* is described in, e.g., Stackebrandt, E. et al. (1995) *Int. J. Syst. Bacteriol.* 45:682-92).

Further AmyNEST polypeptides have a specified degree of amino acid sequence identity to the α-amylase obtained from *N. xinjiangensis* strain B4.2S6. Such AmyNEST polypeptides include naturally-occurring variants, variants that include man-made amino acid substitutions, insertions, or deletions, chimeras, and homologs. In some cases, these AmyNEST polypeptides have at least 57%, at least 60%, at least 65%, at least 70%, at least 75%, at least 80%, at least 81%, 82%, 83%, 84%, 85%, 86%, 87%, 88%, 89%, 90%, 91%, 92%, 93%, 94%, 95%, 96%, 97%, or 98%, or even at least 99% overall homology/identity to the α-amylase obtained from *N. xinjiangensis* strain B4.2S6 (SEQ ID NO: 11).

Yet further AmyNEST polypeptides have a specified degree of overall amino acid sequence identity to the α-amylase obtained from *N. xinjiangensis* strain B4.2S6, while including particular amino acid sequences of the *N. xinjiangensis* strain B4.2S6 polypeptide. For example, the AmyNEST polypeptide may have at least 57%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, or even at least 99% overall amino acid sequence identity with SEQ ID NO: 11, while including the amino acid sequence of carbohydrate binding module (CBM) 25(1) (i.e., SEQ ID NO: 12) and/or CBM 25(2) (i.e., SEQ ID NO: 13). Similarly, the AmyNEST polypeptide may have at least 57%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, or even at least 99% overall amino acid sequence identity with SEQ ID NO: 11, while including an amino acid sequence that has at least 80%, at least 85%, at least 90%, at least 91%, at least 92%, at least 93%, at least 94%, at least 95%, at least 96%, at least 97%, at least 98%, or even at least 99% sequence identity with CBM 25(1) and/or CBM 25(2). The AmyNEST polypeptide may also include an amino acid sequence that has at least 80%, at least 85%, at least 90%, at least 91%, at least 92%, at least 93%, at least 94%, at least 95%, at least 96%, at least 97%, at least 98%, or even at least 99% sequence identity with CBM 25(1) and an amino acid sequence that has at least 80%, at least 85%, at least 90%, at least 91%, at least 92%, at least 93%, at least 94%, at least 95%, at least 96%, at least 97%, at least 98%, or even at least 99% sequence identity with CBM 25(2). The amino acid sequences relating to CBM 25(1) and CBM 25(2) in the AmyNEST polypeptide may be separated by a linker, e.g., having at least 57%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, or even at least 99% amino acid sequence identity with SEQ ID NO: 19.

AmyNEST polypeptides may be a "full-length" ("fl"), "immature," or "precursor" polypeptides, which include a signal sequence, or "mature" polypeptides, which lack the signal sequence. An exemplary immature AmyNEST polypeptide has the amino acid sequences of SEQ ID NO: 9, while an exemplary mature AmyNEST polypeptides has the amino acid sequences of SEQ ID NO: 11. Generally, mature forms of the polypeptides are most active and most useful for cleaning and other applications.

AmyNEST polypeptides may be truncated such that they lack the N or C-terminus of the mature form. One exemplary truncated AmyNEST polypeptide lacks the C-terminal second carbohydrate binding module (CBM) (i.e., CBM (2)) but retain the N-terminal catalytic domain. Another exemplary truncated AmyNEST polypeptide lacks both the C-terminal CBMs (i.e., CBM (1) and CBM (2)) but retains the N-terminal catalytic domain. A related AmyNEST polypeptide lacks CBM (2) but retains CBM (1) and N-terminal catalytic domain AmyNEST polypeptides lacking one or more CBMs are useful where high catalytic turnover is desired, ideally where the concentration of AmyNEST polypeptides is sufficiently high compared to the substrate to be hydrolyzed that the presence of the CBM is not critical to promote enzyme substrate interactions.

Similarly, AmyNEST polypeptides include fragments that retain at least a portion of the α-amylase activity characteristic of the parental AmyNEST polypeptides. Preferred fragments include at least a portion of the catalytic domain As noted above, AmyNEST polypeptides include variant polypeptides, such as those that include man-made substitutions. Exemplary substitutions are conservative amino acid substitutions, such as those listed in the following table.

| For Amino Acid | Code | Replace with any of |
|---|---|---|
| Alanine | A | D-Ala, Gly, beta-Ala, L-Cys, D-Cys |
| Arginine | R | D-Arg, Lys, D-Lys, homo-Arg, D-homo-Arg, Met, Ile, D-Met, D-Ile, Orn, D-Orn |
| Asparagine | N | D-Asn, Asp, D-Asp, Glu, D-Glu, Gln, D-Gln |
| Aspartic Acid | D | D-Asp, D-Asn, Asn, Glu, D-Glu, Gln, D-Gln |
| Cysteine | C | D-Cys, S-Me-Cys, Met, D-Met, Thr, D-Thr |

-continued

| For Amino Acid | Code | Replace with any of |
|---|---|---|
| Glutamine | Q | D-Gln, Asn, D-Asn, Glu, D-Glu, Asp, D-Asp |
| Glutamic Acid | E | D-Glu, D-Asp, Asp, Asn, D-Asn, Gln, D-Gln |
| Glycine | G | Ala, D-Ala, Pro, D-Pro, b-Ala, Acp |
| Isoleucine | I | D-Ile, Val, D-Val, Leu, D-Leu, Met, D-Met |
| Leucine | L | D-Leu, Val, D-Val, Leu, D-Leu, Met, D-Met |
| Lysine | K | D-Lys, Arg, D-Arg, homo-Arg, D-homo-Arg, Met, D-Met, Ile, D-Ile, Orn, D-Orn |
| Methionine | M | D-Met, S-Me-Cys, Ile, D-Ile, Leu, D-Leu, Val, D-Val |
| Phenylalanine | F | D-Phe, Tyr, D-Thr, L-Dopa, His, D-His, Trp, D-Trp, Trans-3,4, or 5-phenylproline, cis-3,4, or 5-phenylproline |
| Proline | P | D-Pro, L-I-thioazolidine-4-carboxylic acid, D-or L-1-oxazolidine-4-carboxylic acid |
| Serine | S | D-Ser, Thr, D-Thr, allo-Thr, Met, D-Met, Met(O), D-Met(O), L-Cys, D-Cys |
| Threonine | T | D-Thr, Ser, D-Ser, allo-Thr, Met, D-Met, Met(O), D-Met(O), Val, D-Val |
| Tyrosine | Y | D-Tyr, Phe, D-Phe, L-Dopa, His, D-His |
| Valine | V | D-Val, Leu, D-Leu, Ile, D-Ile, Met, D-Met |

As before, preferred AmyNEST polypeptides retain α-amylase activity but may have altered biochemical properties with reference to a naturally-occurring parental polypeptide.

The polypeptide may also be a chimeric polypeptide that includes at least a portion of an AmyNEST polypeptides, and at least a portion of a second polypeptide. The second polypeptide may be, for example, a second amylase, a heterologous signal sequence, an epitope to allow tracking or purification, or the like. Exemplary heterologous signal sequences are from B. subtilis amylase (AmyE) or AprE, and Streptomyces CelA.

Another aspect of the present compositions and methods is a nucleic acid encoding an AmyNEST polypeptide. The nucleic acid may encode the AmyNEST polypeptide obtained from N. xinjiangensis strain B4.2S6 or any of the variants, truncated forms, fragments, chimeras, and homologs, described above. In some cases, the nucleic acid encodes an amylase having at least 57%, at least 60%, at least 65%, at least 70%, at least 75%, at least 80%, at least 81%, 82%, 83%, 84%, 85%, 86%, 87%, 88%, 89%, 90%, 91%, 92%, 93%, 94%, 95%, 96%, 97%, or 98%, or even at least 99% homology/identity to AmyNEST polypeptide obtained from N. xinjiangensis strain B4.2S6. Due to the degeneracy of the genetic code, it is understood that a plurality of nucleic acids may encode the same polypeptide.

The nucleic acid may also have a specified degree of nucleotide sequence identity to an exemplary polynucleotide encoding an AmyNEST polypeptide, such as SEQ ID NO: 7 or SEQ ID NO: 8, which encodes the AmyNEST polypeptide obtained from N. xinjiangensis strain B4.2S6. In one example, the nucleic acid has at least 75%, 80%, 85%, 86%, 87%, 88%, 89%, 90%, 91%, 92%, 93%, 94%, 95%, 96%, 97%, 98% or even 99% identity to the polynucleotide of SEQ ID NO: 7 or SEQ ID NO: 8. In another example, the nucleic acid hybridizes under stringent or very stringent conditions to the polynucleotide of SEQ ID NO: 7 or SEA ID NO: 8. The nucleic acids may encode a "full-length" ("fl") or "immature" polypeptide, which includes a signal sequence, or a "mature" polypeptide, which lacks a signal sequence.

A nucleic acid that encodes an AmyNEST polypeptide can be operably linked to various promoters and regulators in a vector for expression in various host cells. A nucleic acid that encodes an AmyNEST polypeptide can also be linked to other coding sequences, e.g., to encode a chimeric polypeptide. Exemplary promoters are the B. subtilis Amy E and AprE promoters, and the Streptomyces CelA promoters.

3. Method of Producing and Purifying Proteins

Methods of producing and purifying proteins that are secreted in to the culture medium from Bacillus are known in the art, as are suitable host cells for producing α-amylases. Exemplary methods for producing the α-amylases are described below.

3.1 Materials and Methods for Producing α-Amylases

An AmyNEST polypeptide can be expressed, in enzyme form, using an expression vector which typically includes control sequences encoding a suitable promoter, operator, ribosome binding site, translation initiation signal, and, optionally, a repressor gene or various activator genes. A large number of vectors are commercially available for use with recombinant DNA procedures, and the choice of vector will often depend on the host cell into which it is to be introduced. The vector may be an autonomously replicating vector, i.e., a vector that exists as an extrachromosomal entity, the replication of which is independent of chromosomal replication, e.g., a plasmid, a bacteriophage or an extrachromosomal element, mini-chromosome or an artificial chromosome. Alternatively, the vector may be one which, when introduced into an isolated host cell, is integrated into the host cell genome and replicated together with the chromosome(s) into which it has been integrated. The integrated gene may also be amplified to create multiple copies of the gene in the chromosome by use of an amplifiable construct driven by antibiotic selection or other selective pressure, such as an essential regulatory gene or by complementation through dose effect of an essential metabolic pathway gene.

In the vector, the DNA sequence should be operably linked to a suitable promoter sequence. The promoter may be any DNA sequence that shows transcriptional activity in the host cell of choice and may be derived from genes encoding proteins either homologous or heterologous to the host cell. Exemplary promoters for directing the transcription of the DNA sequence encoding an AmyNEST polypeptide, especially in a bacterial host, are the promoter of the lac operon of E. coli, the Streptomyces coelicolor agarase gene dagA or celA promoters, the promoters of the Bacillus licheniformis α-amylase gene (amyL), the promoters of the Geobacillus (formerly Bacillus) stearothermophilus maltogenic amylase gene (amyM), the promoters of the Bacillus amyloliquefaciens α-amylase (amyQ), the promoters of the Bacillus subtilis xylA and xylB genes, etc. For transcription in a fungal host, examples of useful promoters are those derived from the gene encoding Aspergillus oryzae TAKA amylase, Rhizomucor miehei aspartic proteinase, Aspergillus niger neutral α-amylase, A. niger acid stable α-amylase, A. niger glucoamylase, Rhizomucor miehei lipase, A. oryzae alkaline protease, A. oryzae triose phosphate isomerase, or A. nidulans acetamidase. When a gene encoding an AmyNEST polypeptide is expressed in a bacterial species such as E. coli, a suitable promoter can be selected, for example, from a bacteriophage promoter including a T7 promoter and a phage lambda promoter. Examples of suitable promoters for the expression in a yeast species include but are not limited to the Gal 1 and Gal 10 promoters of Saccharomyces cerevisiae and the Pichia pastoris AOX1 or AOX2 promoters. For expression in Trichoderma reesei, the CBHII (cellobiohydrolase II) promoter may be used.

An expression vector may also comprise a suitable transcription terminator and, in eukaryotes, polyadenylation sequences operably linked to the DNA sequence encoding an AmyNEST polypeptide. Termination and polyadenylation sequences may suitably be derived from the same sources as the promoter.

The vector may further comprise a DNA sequence enabling the vector to replicate in the host cell. Examples of such sequences are the origins of replication of plasmids pUC19, pACYC177, pUB110, pE194, pAMB1, and pIJ702.

The vector may also comprise a selectable marker, e.g., a gene the product of which complements a defect in the isolated host cell, such as the dal genes from *B. subtilis* or *B. licheniformis*, or a gene that confers antibiotic resistance such as, e.g., ampicillin, kanamycin, chloramphenicol or tetracycline resistance. Furthermore, the vector may comprise *Aspergillus* selection markers such as amdS, argB, niaD and xxsC, a marker giving rise to hygromycin resistance, or the selection may be accomplished by co-transformation, such as known in the art. See e.g., International PCT Application WO 91/17243.

While intracellular expression or solid-state fermentation may be advantageous in some respects, e.g., when using certain bacteria or fungi as host cells, one aspect contemplates expression of an AmyNEST polypeptide into the culture medium. In general, the α-amylase comprises a signal sequence at the amino terminus that permits secretion into the culture medium. If desirable, this signal peptide may be replaced by a different sequence, conveniently accomplished by substitution of the DNA sequences encoding the respective signal polypeptide.

Figure 5:
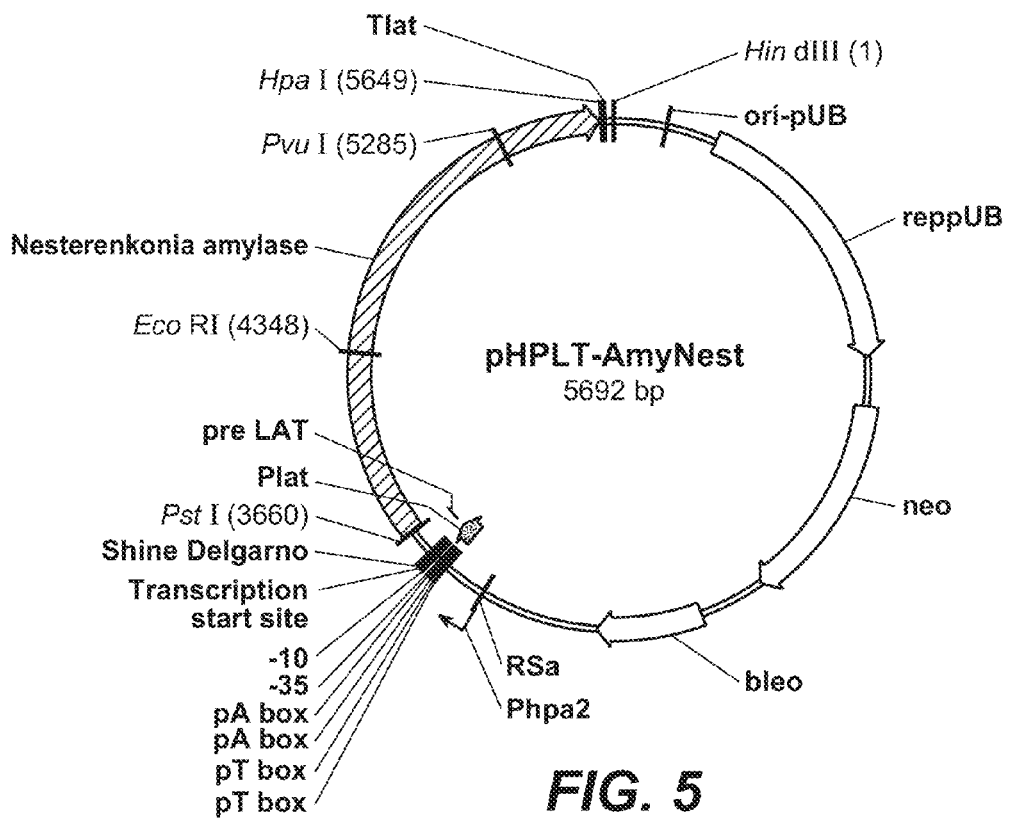
FIG. 5 is a plasmid map of pHPLT-AmyNEST.

The expression vector typically includes the components of a cloning vector, such as, for example, an element that permits autonomous replication of the vector in the selected host organism and one or more phenotypically detectable markers for selection purposes. The expression vector normally comprises control nucleotide sequences such as a promoter, operator, ribosome binding site, translation initiation signal and optionally, a repressor gene or one or more activator genes. Additionally, the expression vector may comprise a sequence coding for an amino acid sequence capable of targeting the AmyNEST polypeptide to a host cell organelle such as a peroxisome, or to a particular host cell compartment. Such a targeting sequence includes but is not limited to the sequence, SKL. For expression under the direction of control sequences, the nucleic acid sequence of the AmyNEST polypeptide is operably linked to the control sequences in proper manner with respect to expression. An exemplary vector is depicted in FIG. 5.

The procedures used to ligate the DNA construct encoding an AmyNEST polypeptide, the promoter, terminator and other elements, respectively, and to insert them into suitable vectors containing the information necessary for replication, are well known to persons skilled in the art (see e.g., Sambrook et al., MOLECULAR CLONING: A LABORATORY MANUAL, $2^{nd}$ ed., Cold Spring Harbor, 1989, and $3^{rd}$ ed., 2001).

An isolated cell, either comprising a DNA construct or an expression vector, is advantageously used as a host cell in the recombinant production of an AmyNEST polypeptide. The cell may be transformed with the DNA construct encoding the enzyme, conveniently by integrating the DNA construct (in one or more copies) in the host chromosome. This integration is generally considered to be an advantage, as the DNA sequence is more likely to be stably maintained in the cell. Integration of the DNA constructs into the host chromosome may be performed according to conventional methods, e.g., by homologous or heterologous recombination. Alternatively, the cell may be transformed with an expression vector as described above in connection with the different types of host cells.

Examples of suitable bacterial host organisms are Gram positive bacterial species such as *Bacillaceae* including *Bacillus subtilis*, *Bacillus licheniformis*, *Bacillus lentus*, *Bacillus brevis*, *Geobacillus* (formerly *Bacillus*) *stearothermophilus*, *Bacillus alkalophilus*, *Bacillus amyloliquefaciens*, *Bacillus coagulans*, *Bacillus lautus*, *Bacillus megaterium*, and *Bacillus thuringiensis*; *Streptomyces* species such as *Streptomyces murinus*; lactic acid bacterial species including *Lactococcus* spp. such as *Lactococcus lactis*; *Lactobacillus* spp. including *Lactobacillus reuteri*; *Leuconostoc* spp.; *Pediococcus* spp.; and *Streptococcus* spp. Alternatively, strains of a Gram negative bacterial species belonging to Enterobacteriaceae including *E. coli*, or to Pseudomonadaceae can be selected as the host organism.

A suitable yeast host organism can be selected from the biotechnologically relevant yeasts species such as but not limited to yeast species such as *Pichia* sp., *Hansenula* sp., or *Kluyveromyces*, *Yarrowinia*, *Schizosaccharomyces* species or a species of *Saccharomyces*, including *Saccharomyces cerevisiae* or a species belonging to *Schizosaccharomyces* such as, for example, *S. pombe* species. A strain of the methylotrophic yeast species, *Pichia pastoris*, can be used as the host organism. Alternatively, the host organism can be a *Hansenula* species. Suitable host organisms among filamentous fungi include species of *Aspergillus*, e.g., *Aspergillus niger*, *Aspergillus oryzae*, *Aspergillus tubigensis*, *Aspergillus awamori*, or *Aspergillus nidulans*. Alternatively, strains of a *Fusarium* species, e.g., *Fusarium oxysporum* or of a *Rhizomucor* species such as *Rhizomucor miehei* can be used as the host organism. Other suitable strains include *Thermomyces* and *Mucor* species. In addition, *Trichoderma reesei* can be used as a host. A suitable procedure for transformation of *Aspergillus* host cells includes, for example, that described in EP 238023.

In a yet further aspect, a method of producing an AmyNEST polypeptide is provided comprising cultivating a host cell as described above under conditions conducive to the production of the enzyme and recovering the enzyme from the cells and/or culture medium.

The medium used to cultivate the cells may be any conventional medium suitable for growing the host cell in question and obtaining expression of an AmyNEST polypeptide. Suitable media and media components are available from commercial suppliers or may be prepared according to published recipes (e.g., as described in catalogues of the American Type Culture Collection).

In one aspect, an enzyme secreted from the host cells is used in a whole broth preparation. In the present methods, the preparation of a spent whole fermentation broth of a recombinant microorganism can be achieved using any cultivation method known in the art resulting in the expression of an α-amylase. Fermentation may, therefore, be understood as comprising shake flask cultivation, small- or large-scale fermentation (including continuous, batch, fed-batch, or solid state fermentations) in laboratory or industrial fermenters performed in a suitable medium and under conditions allowing the amylase to be expressed or isolated. The term "spent whole fermentation broth" is defined herein as unfractionated contents of fermentation material that includes culture medium, extracellular proteins (e.g., enzymes), and cellular biomass. It is understood that the term "spent whole fermentation broth" also encompasses cellular biomass that has been lysed or permeabilized using methods well known in the art.

An enzyme secreted from the host cells may conveniently be recovered from the culture medium by well-known procedures, including separating the cells from the medium by centrifugation or filtration, and precipitating proteinaceous components of the medium by means of a salt such as ammonium sulfate, followed by the use of chromatographic procedures such as ion exchange chromatography, affinity chromatography, or the like.

An aspect contemplates the polynucleotide in a vector is operably linked to a control sequence that is capable of providing for the expression of the coding sequence by the host cell, i.e. the vector is an expression vector. The control sequences may be modified, for example by the addition of further transcriptional regulatory elements to make the level of transcription directed by the control sequences more responsive to transcriptional modulators. The control sequences may in particular comprise promoters.

Host cells may be cultured under suitable conditions that allow expression of an AmyNEST polypeptide. Expression of the enzymes may be constitutive such that they are continually produced, or inducible, requiring a stimulus to initiate expression. In the case of inducible expression, protein production can be initiated when required by, for example, addition of an inducer substance to the culture medium, for example dexamethasone or IPTG or Sopharose. Polypeptides can also be produced recombinantly in an in vitro cell-free system, such as the TNT™ (Promega) rabbit reticulocyte system.

An AmyNEST polypeptide-expressing host also can be cultured in the appropriate medium for the host, under aerobic conditions. Shaking or a combination of agitation and aeration can be provided, with production occurring at the appropriate temperature for that host, e.g., from about 25° C. to about 75° C. (e.g., 30° C. to 45° C.), depending on the needs of the host and production of the desired AmyNEST polypeptide. Culturing can occur from about 12 to about 100 hours or greater (and any hour value there between, e.g., from 24 to 72 hours). Typically, the culture broth is at a pH of about 5.5 to about 8.0, again depending on the culture conditions needed for the host relative to production of an AmyNEST polypeptide.

3.2 Materials and Methods for Protein Purification

Fermentation, separation, and concentration techniques are well known in the art and conventional methods can be used in order to prepare a concentrated AmyNEST polypeptide-containing solution.

After fermentation, a fermentation broth is obtained, the microbial cells and various suspended solids, including residual raw fermentation materials, are removed by conventional separation techniques in order to obtain an amylase solution. Filtration, centrifugation, microfiltration, rotary vacuum drum filtration, ultrafiltration, centrifugation followed by ultra-filtration, extraction, or chromatography, or the like, are generally used.

It is desirable to concentrate an AmyNEST polypeptide-containing solution in order to optimize recovery. Use of unconcentrated solutions requires increased incubation time in order to collect the purified enzyme precipitate.

The enzyme containing solution is concentrated using conventional concentration techniques until the desired enzyme level is obtained. Concentration of the enzyme containing solution may be achieved using any of the techniques discussed herein or otherwise known in the art. Exemplary methods of concentration include but are not limited to rotary vacuum filtration and/or ultrafiltration.

Concentration may be performed using e.g., a precipitation agent, such as a metal halide precipitation agent. Metal halide precipitation agents include but are not limited to alkali metal chlorides, alkali metal bromides and blends of two or more of these metal halides. Exemplary metal halides include sodium chloride, potassium chloride, sodium bromide, potassium bromide and blends of two or more of these metal halides. The metal halide precipitation agent, sodium chloride, can also be used as a preservative.

The metal halide precipitation agent is used in an amount effective to precipitate the AmyNEST polypeptide. The selection of at least an effective amount and an optimum amount of metal halide effective to cause precipitation of the enzyme, as well as the conditions of the precipitation for maximum recovery including incubation time, pH, temperature and concentration of enzyme, will be readily apparent to one of ordinary skill in the art, after routine testing.

Generally, at least about 5% w/v (weight/volume) to about 25% w/v of metal halide is added to the concentrated enzyme solution, and usually at least 8% w/v. Generally, no more than about 25% w/v of metal halide is added to the concentrated enzyme solution and usually no more than about 20% w/v. The optimal concentration of the metal halide precipitation agent will depend, among others, on the nature of the specific AmyNEST polypeptide and on its concentration in the concentrated enzyme solution.

Another alternative to effect precipitation of the enzyme is to use organic compounds. Exemplary organic compound precipitating agents include: 4-hydroxybenzoic acid, alkali metal salts of 4-hydroxybenzoic acid, alkyl esters of 4-hydroxybenzoic acid, and blends of two or more of these organic compounds. The addition of said organic compound precipitation agents can take place prior to, simultaneously with or subsequent to the addition of the metal halide precipitation agent, and the addition of both precipitation agents, organic compound and metal halide, may be carried out sequentially or simultaneously.

Generally, the organic precipitation agents are selected from the group consisting of alkali metal salts of 4-hydroxybenzoic acid, such as sodium or potassium salts, and linear or branched alkyl esters of 4-hydroxybenzoic acid, wherein the alkyl group contains from 1 to 12 carbon atoms, and blends of two or more of these organic compounds. The organic compound precipitation agents can be, for example, linear or branched alkyl esters of 4-hydroxybenzoic acid, wherein the alkyl group contains from 1 to 10 carbon atoms, and blends of two or more of these organic compounds. Exemplary organic compounds are linear alkyl esters of 4-hydroxybenzoic acid, wherein the alkyl group contains from 1 to 6 carbon atoms, and blends of two or more of these organic compounds. Methyl esters of 4-hydroxybenzoic acid, propyl esters of 4-hydroxybenzoic acid, butyl ester of 4-hydroxybenzoic acid, ethyl ester of 4-hydroxybenzoic acid and blends of two or more of these organic compounds can also be used. Additional organic compounds also include but are not limited to 4-hydroxybenzoic acid methyl ester (named methyl PARABEN), 4-hydroxybenzoic acid propyl ester (named propyl PARABEN), which also are both amylase preservative agents. For further descriptions, see, e.g., U.S. Pat. No. 5,281,526.

Addition of the organic compound precipitation agent provides the advantage of high flexibility of the precipitation conditions with respect to pH, temperature, AmyNEST polypeptide concentration, precipitation agent concentration, and time of incubation.

The organic compound precipitation agent is used in an amount effective to improve precipitation of the enzyme by means of the metal halide precipitation agent. The selection of at least an effective amount and an optimum amount of organic compound precipitation agent, as well as the conditions of the precipitation for maximum recovery including incubation time, pH, temperature and concentration of enzyme, will be readily apparent to one of ordinary skill in the art, in light of the present disclosure, after routine testing.

Generally, at least about 0.01% w/v of organic compound precipitation agent is added to the concentrated AmyNEST-related polypeptide solution and usually at least about 0.02% w/v. Generally, no more than about 0.3% w/v of organic compound precipitation agent is added to the concentrated AmyNEST polypeptide solution and usually no more than about 0.2% w/v.

The concentrated enzyme solution, containing the metal halide precipitation agent, and the organic compound precipitation agent, can be adjusted to a pH, which will, of necessity, depend on the enzyme to be purified. Generally, the pH is adjusted at a level near the isoelectric point of the amylase. The pH can be adjusted at a pH in a range from about 2.5 pH units below the isoelectric point (pI) up to about 2.5 pH units above the isoelectric point.

The incubation time necessary to obtain a purified enzyme precipitate depends on the nature of the specific enzyme, the concentration of enzyme, and the specific precipitation agent(s) and its (their) concentration. Generally, the time effective to precipitate the enzyme is between about 1 to about 30 hours; usually it does not exceed about 25 hours. In the presence of the organic compound precipitation agent, the time of incubation can still be reduced to less about 10 hours and in most cases even about 6 hours.

Generally, the temperature during incubation is between about 4° C. and about 50° C. Usually, the method is carried out at a temperature between about 10° C. and about 45° C. (e.g., between about 20° C. and about 40° C.). The optimal temperature for inducing precipitation varies according to the solution conditions and the enzyme or precipitation agent(s) used.

The overall recovery of purified enzyme precipitate, and the efficiency with which the process is conducted, is improved by agitating the solution comprising the enzyme, the added metal halide and the added organic compound. The agitation step is done both during addition of the metal halide and the organic compound, and during the subsequent incubation period. Suitable agitation methods include mechanical stirring or shaking, vigorous aeration, or any similar technique.

After the incubation period, the purified enzyme is then separated from the dissociated pigment and other impurities and collected by conventional separation techniques, such as filtration, centrifugation, microfiltration, rotary vacuum filtration, ultrafiltration, press filtration, cross membrane microfiltration, cross flow membrane microfiltration, or the like. Further purification of the purified enzyme precipitate can be obtained by washing the precipitate with water. For example, the purified enzyme precipitate is washed with water containing the metal halide precipitation agent, or with water containing the metal halide and the organic compound precipitation agents.

During fermentation, an AmyNEST polypeptide accumulates in the culture broth. For the isolation and purification of the desired AmyNEST polypeptide, the culture broth is centrifuged or filtered to eliminate cells, and the resulting cell-free liquid is used for enzyme purification. In one embodiment, the cell-free broth is subjected to salting out using ammonium sulfate at about 70% saturation; the 70% saturation-precipitation fraction is then dissolved in a buffer and applied to a column such as a Sephadex G-100 column, and eluted to recover the enzyme-active fraction. For further purification, a conventional procedure such as ion exchange chromatography may be used.

Purified enzymes are useful for laundry and cleaning applications. For example, they can be used in laundry detergents and spot removers. They can be made into a final product that is either liquid (solution, slurry) or solid (granular, powder).

A more specific example of purification, is described in Sumitani, J. et al. (2000) *Biochem. J.* 350: 477-484 and is briefly summarized here. The enzyme obtained from 4 liters of a *Streptomyces lividans* TK24 culture supernatant was treated with $(NH_4)_2SO_4$ at 80% saturation. The precipitate was recovered by centrifugation at 10,000×g (20 minutes and 4° C.) and re-dissolved in 20 mM Tris/HCl buffer (pH 7.0) containing 5 mM $CaCl_2$. The solubilized precipitate was then dialyzed against the same buffer. The dialyzed sample was then applied to a Sephacryl S-200 column, which had previously been equilibrated with 20 mM Tris/HCl buffer, (pH 7.0), 5 mM $CaCl_2$, and eluted at a linear flow rate of 7 cm/hr with the same buffer. Fractions from the column were collected and assessed for activity as judged by enzyme assay and SDS-PAGE. The protein was further purified as follows. A Toyopearl HW55 column (Tosoh Bioscience, Montgomeryville, Pa.; Cat. No. 19812) was equilibrated with 20 mM Tris/HCl buffer (pH 7.0) containing 5 mM $CaCl_2$ and 1.5 M $(NH_4)_2SO_4$. The enzyme was eluted with a linear gradient of 1.5 to 0 M $(NH_4)_2SO_4$ in 20 mM Tris/HCL buffer, pH 7.0 containing 5 mM $CaCl_2$. The active fractions were collected, and the enzyme precipitated with $(NH_4)_2SO_4$ at 80% saturation. The precipitate was recovered, re-dissolved, and dialyzed as described above. The dialyzed sample was then applied to a Mono Q HR5/5 column (Amersham Pharmacia; Cat. No. 17-5167-01) previously equilibrated with 20 mM Tris/HCl buffer (pH 7.0) containing 5 mM $CaCl_2$, at a flow rate of 60 mL/hour. The active fractions are collected and added to a 1.5 M $(NH_4)_2SO_4$ solution. The active enzyme fractions were re-chromatographed on a Toyopearl HW55 column, as before, to yield a homogeneous enzyme as determined by SDS-PAGE. See J. Sumitani et al., "New type of starch-binding domain: the direct repeat motif in the C-terminal region of *Bacillus* sp. no. 195 α-amylase contributes to starch binding and raw starch degrading," *Biochem. J.* 350: 477-484 (2000) for general discussion of the method and variations thereon.

For production scale recovery, an AmyNEST polypeptide can be partially purified as generally described above by removing cells via flocculation with polymers. Alternatively, the enzyme can be purified by microfiltration followed by concentration by ultrafiltration using available membranes and equipment. However, for some applications, the enzyme does not need to be purified, and whole broth culture can be lysed and used without further treatment. The enzyme can then be processed, for example, into granules.

4. Cleaning Compositions

An aspect of the present compositions and methods is a cleaning composition that includes an AmyNEST polypeptide as a component. An AmyNEST polypeptide can be used as a component in detergent compositions for hand washing, laundry washing, dishwashing, and other hard-surface cleaning. Preferably, an AmyNEST polypeptide is incorporated into detergents at or near a concentration conventionally used for amylase in detergents. For example, an AmyNEST polypeptide may be added in amount corresponding to 0.00001-1 mg (calculated as pure enzyme protein) of α-amylase per liter of wash/dishwash liquor. Exemplary formulations are provided herein, as exemplified by the following:

4.1 Laundry Detergent Composition

An AmyNEST polypeptide may typically be a component of a detergent composition, as the only enzyme or with other enzymes including other amylolytic enzymes. As such, it may be included in the detergent composition in the form of a non-dusting granulate, a stabilized liquid, or a protected enzyme. Non-dusting granulates may be produced, e.g., as disclosed in U.S. Pat. Nos. 4,106,991 and 4,661,452 and may optionally be coated by methods known in the art. Examples of waxy coating materials are poly(ethylene oxide) products (polyethyleneglycol, PEG) with mean molar weights of 1,000 to 20,000; ethoxylated nonylphenols having from 16 to 50 ethylene oxide units; ethoxylated fatty alcohols in which the alcohol contains from 12 to 20 carbon atoms and in which there are 15 to 80 ethylene oxide units; fatty alcohols; fatty acids; and mono- and di- and triglycerides of fatty acids. Examples of film-forming coating materials suitable for application by fluid bed techniques are given in, for example, GB Patent No. 1483591. Liquid enzyme preparations may, for instance, be stabilized by adding a polyol such as propylene glycol, a sugar or sugar alcohol, lactic acid or boric acid according to established methods. Other enzyme stabilizers are well known in the art. Protected enzymes may be prepared according to the method disclosed in for example EP 238,216. Polyols have long been recognized as stabilizers of proteins, as well as improving protein solubility. See, e.g., Kaushik, J. K. et al. (2003) *J. Biol. Chem.* 278: 26458-65 and references cited therein; and Monica Conti, M. et al. (1997) *J. Chromatography A* 757: 237-245.

The detergent composition may be in any useful form, e.g., as powders, granules, pastes, or liquid. A liquid detergent may be aqueous, typically containing up to about 70% of water and 0% to about 30% of organic solvent. It may also be in the form of a compact gel type containing only about 30% water.

The detergent composition comprises one or more surfactants, each of which may be anionic, nonionic, cationic, or zwitterionic. The detergent will usually contain 0% to about 50% of anionic surfactant, such as linear alkylbenzenesulfonate (LAS); α-olefinsulfonate (AOS); alkyl sulfate (fatty alcohol sulfate) (AS); alcohol ethoxysulfate (AEOS or AES); secondary alkanesulfonates (SAS); α-sulfo fatty acid methyl esters; alkyl- or alkenylsuccinic acid; or soap. The composition may also contain 0% to about 40% of nonionic surfactant such as alcohol ethoxylate (AEO or AE), carboxylated alcohol ethoxylates, nonylphenol ethoxylate, alkylpolyglycoside, alkyldimethylamineoxide, ethoxylated fatty acid monoethanolamide, fatty acid monoethanolamide, or polyhydroxy alkyl fatty acid amide (as described for example in WO 92/06154).

The detergent composition may additionally comprise one or more other enzymes, such as lipase, another amylolytic enzyme, cutinase, protease, cellulase, peroxidase, and/or laccase in any combination.

The detergent may contain about 1% to about 65% of a detergent builder or complexing agent such as zeolite, diphosphate, triphosphate, phosphonate, citrate, nitrilotriacetic acid (NTA), ethylenediaminetetraacetic acid (EDTA), diethylenetriaminepentaacetic acid (DTMPA), alkyl- or alkenylsuccinic acid, soluble silicates or layered silicates (e.g., SKS-6 from Hoechst). The detergent may also be unbuilt, i.e. essentially free of detergent builder. The enzymes can be used in any composition compatible with the stability of the enzyme. Enzymes generally can be protected against deleterious components by known forms of encapsulation, for example, by granulation or sequestration in hydro gels. Enzymes, and specifically α-amylases, such as AmyNEST polypeptides, either with or without CBDs, can be used in a variety of compositions including laundry and dishwashing applications, surface cleaners, as well as in compositions for ethanol production from starch or biomass.

The detergent may comprise one or more polymers. Examples include carboxymethylcellulose (CMC), poly(vinylpyrrolidone) (PVP), polyethyleneglycol (PEG), poly(vinyl alcohol) (PVA), polycarboxylates such as polyacrylates, maleic/acrylic acid copolymers and lauryl methacrylate/acrylic acid copolymers.

The detergent may contain a bleaching system, which may comprise a $H_2O_2$ source such as perborate or percarbonate, which may be combined with a peracid-forming bleach activator such as tetraacetylethylenediamine (TAED) or nonanoyloxybenzenesulfonate (NOBS). Alternatively, the bleaching system may comprise peroxyacids (e.g., the amide, imide, or sulfone type peroxyacids). The bleaching system can also be an enzymatic bleaching system, for example, perhydrolase, such as that described in International PCT Application WO 2005/056783.

The enzymes of the detergent composition may be stabilized using conventional stabilizing agents, e.g., a polyol such as propylene glycol or glycerol; a sugar or sugar alcohol; lactic acid; boric acid or a boric acid derivative such as, e.g., an aromatic borate ester; and the composition may be formulated as described in, e.g., WO 92/19709 and WO 92/19708.

The detergent may also contain other conventional detergent ingredients such as e.g., fabric conditioners including clays, foam boosters, suds suppressors, anti-corrosion agents, soil-suspending agents, anti-soil redeposition agents, dyes, bactericides, tarnish inhibitors, optical brighteners, or perfumes.

The pH (measured in aqueous solution at use concentration) is usually neutral or alkaline, e.g., pH about 7.0 to about 11.0.

Particular forms of detergent compositions comprising the AmyNEST-related polypeptides can be formulated to include:

1) A detergent composition formulated as a granulate having a bulk density of at least 600 g/L comprising linear alkylbenzenesulfonate (calculated as acid) about 7% to about 12%; alcohol ethoxysulfate (e.g., $C_{12-18}$ alcohol, 1-2 ethylene oxide (EO)) or alkyl sulfate (e.g., $C_{16-18}$) about 1% to about 4%; alcohol ethoxylate (e.g., $C_{14-15}$ alcohol, 7 EO) about 5% to about 9%; sodium carbonate (e.g., $Na_2CO_3$) about 14% to about 20%; soluble silicate (e.g., $Na_2O$, $2SiO_2$) about 2 to about 6%; zeolite (e.g., $NaAlSiO_4$) about 15% to about 22%; sodium sulfate (e.g., $Na_2SO_4$) 0% to about 6%; sodium citrate/citric acid (e.g., $C_6H_5Na_3O_7/C_6H_8O_7$) about 0% to about 15%; sodium perborate (e.g., $NaBO_3H_2O$) about 11% to about 18%; TAED about 2% to about 6%; carboxymethylcellulose (CMC) and 0% to about 2%; polymers (e.g., maleic/acrylic acid, copolymer, PVP, PEG) 0-3%; enzymes (calculated as pure enzyme) 0.0001-0.1% protein; and minor ingredients (e.g., suds suppressors, perfumes, optical brightener, photobleach) 0-5%.

2) A detergent composition formulated as a granulate having a bulk density of at least 600 g/L comprising linear alkylbenzenesulfonate (calculated as acid) about 6% to about 11%; alcohol ethoxysulfate (e.g., $C_{12-18}$ alcohol, 1-2 EO) or alkyl sulfate (e.g., $C_{16-18}$) about 1% to about 3%; alcohol ethoxylate (e.g., $C_{14-15}$ alcohol, 7 EO) about 5% to about 9%; sodium carbonate (e.g., $Na_2CO_3$) about 15% to about 21%; soluble silicate (e.g., $Na_2O$, $2SiO_2$) about 1% to about 4%; zeolite (e.g., $NaAlSiO_4$) about 24% to about 34%; sodium sulfate (e.g., $Na_2SO_4$) about 4% to about 10%; sodium citrate/citric acid (e.g., $C_6H_5Na_3O_7/C_6H_8O_7$) 0% to about 15%; carboxymethylcellulose (CMC) 0% to about 2%; polymers (e.g., maleic/acrylic acid copolymer, PVP, PEG) 1-6%; enzymes (calculated as pure enzyme protein) 0.0001-0.1%; minor ingredients (e.g., suds suppressors, perfume) 0-5%.

3) A detergent composition formulated as a granulate having a bulk density of at least 600 g/L comprising linear alkylbenzenesulfonate (calculated as acid) about 5% to about 9%; alcohol ethoxylate (e.g., $C_{12-15}$ alcohol, 7 EO) about 7% to about 14%; Soap as fatty acid (e.g., $C_{16-22}$ fatty acid) about 1 to about 3%; sodium carbonate (as $Na_2CO_3$) about 10% to about 17%; soluble silicate (e.g., $Na_2O$, $2SiO_2$) about 3% to about 9%; zeolite (as $NaAlSiO_4$) about 23% to about 33%; sodium sulfate (e.g., $Na_2SO_4$) 0% to about 4%; sodium perborate (e.g., $NaBO_3H_2O$) about 8% to about 16%; TAED about 2% to about 8%; phosphonate (e.g., EDTMPA) 0% to about 1%; carboxymethylcellulose (CMC) 0% to about 2%; polymers (e.g., maleic/acrylic acid copolymer, PVP, PEG) 0-3%; enzymes (calculated as pure enzyme protein) 0.0001-0.1%; minor ingredients (e.g., suds suppressors, perfume, optical brightener) 0-5%.

4) A detergent composition formulated as a granulate having a bulk density of at least 600 g/L comprising linear alkylbenzenesulfonate (calculated as acid) about 8% to about 12%; alcohol ethoxylate (e.g., $C_{12-15}$ alcohol, 7 EO) about 10% to about 25%; sodium carbonate (as $Na_2CO_3$) about 14% to about 22%; soluble silicate (e.g., $Na_2O$, $2SiO_2$) about 1% to about 5%; zeolite (e.g., $NaAlSiO_4$) about 25% to about 35%; sodium sulfate (e.g., $Na_2SO_4$) 0% to about 10%; carboxymethylcellulose (CMC) 0% to about 2%; polymers (e.g., maleic/acrylic acid copolymer, PVP, PEG) 1-3%; enzymes (calculated as pure enzyme protein) 0.0001-0.1%; and minor ingredients (e.g., suds suppressors, perfume) 0-5%.

5) An aqueous liquid detergent composition comprising linear alkylbenzenesulfonate
(calculated as acid) about 15% to about 21%; alcohol ethoxylate (e.g., $C_{12-15}$ alcohol, 7 EO or $C_{12-15}$ alcohol, 5 EO) about 12% to about 18%; soap as fatty acid (e.g., oleic acid) about 3% to about 13%; alkenylsuccinic acid ($C_{12-14}$) 0% to about 13%; aminoethanol about 8% to about 18%; citric acid about 2% to about 8%; phosphonate 0% to about 3%; polymers (e.g., PVP, PEG) 0% to about 3%; borate (e.g., $B_4O_7$) 0% to about 2%; ethanol 0% to about 3%; propylene glycol about 8% to about 14%; enzymes (calculated as pure enzyme protein) 0.0001-0.1%; and minor ingredients (e.g., dispersants, suds suppressors, perfume, optical brightener) 0-5%.

6) An aqueous structured liquid detergent composition comprising linear alkylbenzenesulfonate (calculated as acid) about 15% to about 21%; alcohol ethoxylate (e.g., $C_{12-15}$ alcohol, 7 EO, or $C_{12-15}$ alcohol, 5 EO) 3-9%; soap as fatty acid (e.g., oleic acid) about 3% to about 10%; zeolite (as $NaAlSiO_4$) about 14% to about 22%; potassium citrate about 9% to about 18%; borate (e.g., $B_4O_7$) 0% to about 2%; carboxymethylcellulose (CMC) 0% to about 2%; polymers (e.g., PEG, PVP) 0% to about 3%; anchoring polymers such as, e.g., lauryl methacrylate/acrylic acid copolymer; molar ratio 25:1, MW 3800) 0% to about 3%; glycerol 0% to about 5%; enzymes (calculated as pure enzyme protein) 0.0001-0.1%; and minor ingredients (e.g., dispersants, suds suppressors, perfume, optical brighteners) 0-5%.

7) A detergent composition formulated as a granulate having a bulk density of at least 600 g/L comprising fatty alcohol sulfate about 5% to about 10%; ethoxylated fatty acid monoethanolamide about 3% to about 9%; soap as fatty acid 0-3%; sodium carbonate (e.g., $Na_2CO_3$) about 5% to about 10%; Soluble silicate (e.g., $Na_2O$, $2SiO_2$) about 1% to about 4%; zeolite (e.g., $NaAlSiO_4$) about 20% to about 40%; Sodium sulfate (e.g., $Na_2SO_4$) about 2% to about 8%; sodium perborate (e.g., $NaBO_3H_2O$) about 12% to about 18%; TAED 2% to about 7%; polymers (e.g., maleic/acrylic acid copolymer, PEG) about 1% to about 5%; enzymes (calculated as pure enzyme protein) 0.0001-0.1%; and minor ingredients (e.g., optical brightener, suds suppressors, perfume) 0-5%.

8) A detergent composition formulated as a granulate comprising linear alkylbenzenesulfonate (calculated as acid) about 8% to about 14%; ethoxylated fatty acid monoethanolamide about 5% to about 11%; soap as fatty acid 0% to about 3%; sodium carbonate (e.g., $Na_2CO_3$) about 4% to about 10%; soluble silicate ($Na_2O$, $2SiO_2$) about 1% to about 4%; zeolite (e.g., $NaAlSiO_4$) about 30% to about 50%; sodium sulfate (e.g., $Na_2SO_4$) about 3% to about 11%; sodium citrate (e.g., $C_6H_5Na_3O_7$) about 5% to about 12%; polymers (e.g., PVP, maleic/acrylic acid copolymer, PEG) about 1% to about 5%; enzymes (calculated as pure enzyme protein) 0.0001-0.1%; and minor ingredients (e.g., suds suppressors, perfume) 0-5%.

9) A detergent composition formulated as a granulate comprising linear alkylbenzenesulfonate (calculated as acid) about 6% to about 12%; nonionic surfactant about 1% to about 4%; soap as fatty acid about 2% to about 6%; sodium carbonate (e.g., $Na_2CO_3$) about 14% to about 22%; zeolite (e.g., $NaAlSiO_4$) about 18% to about 32%; sodium sulfate (e.g., $Na_2SO_4$) about 5% to about 20%; sodium citrate (e.g., $C_6H_5Na_3O_7$) about 3% to about 8%; sodium perborate (e.g., $NaBO_3H_2O$) about 4% to about 9%; bleach activator (e.g., NOBS or TAED) about 1% to about 5%; carboxymethylcellulose (CMC) 0% to about 2%; polymers (e.g., polycarboxylate or PEG) about 1% to about 5%; enzymes (calculated as pure enzyme protein) 0.0001-0.1%; and minor ingredients (e.g., optical brightener, perfume) 0-5%.

10) An aqueous liquid detergent composition comprising linear alkylbenzenesulfonate (calculated as acid) about 15% to about 23%; alcohol ethoxysulfate (e.g., $C_{12-15}$ alcohol, 2-3 EO) about 8% to about 15%; alcohol ethoxylate (e.g., $C_{12-15}$ alcohol, 7 EO, or $C_{12-15}$ alcohol, 5 EO) about 3% to about 9%; soap as fatty acid (e.g., lauric acid) 0% to about 3%; aminoethanol about 1% to about 5%; sodium citrate about 5% to about 10%; hydrotrope (e.g., sodium toluensulfonate) about 2% to about 6%; borate (e.g., $B_4O_7$) 0% to about 2%; carboxymethylcellulose 0% to about 1%; ethanol about 1% to about 3%; propylene glycol about 2% to about 5%; enzymes (calculated as pure enzyme protein) 0.0001-0.1%; and minor ingredients (e.g., polymers, dispersants, perfume, optical brighteners) 0-5%.

11) An aqueous liquid detergent composition comprising linear alkylbenzenesulfonate (calculated as acid) about 20% to about 32%; alcohol ethoxylate (e.g., $C_{12-15}$ alcohol, 7 EO, or $C_{12-15}$ alcohol, 5 EO) 6-12%; aminoethanol about 2% to about 6%; citric acid about 8% to about 14%; borate (e.g., $B_4O_7$) about 1% to about 3%; polymer (e.g., maleic/acrylic acid copolymer, anchoring polymer such as, e.g., lauryl methacrylate/acrylic acid copolymer) 0% to about 3%; glycerol about 3% to about 8%; enzymes (calculated as pure enzyme protein) 0.0001-0.1%; and minor ingredients (e.g., hydrotropes, dispersants, perfume, optical brighteners) 0-5%.

12) A detergent composition formulated as a granulate having a bulk density of at least 600 g/L comprising anionic surfactant (linear alkylbenzenesulfonate, alkyl sulfate, α-olefinsulfonate, α-sulfo fatty acid methyl esters, alkanesulfonates, soap) about 25% to about 40%; nonionic surfactant (e.g., alcohol ethoxylate) about 1% to about 10%; sodium carbonate (e.g., $Na_2CO_3$) about 8% to about 25%; soluble silicates (e.g., $Na_2O$, $2SiO_2$) about 5% to about 15%; sodium sulfate (e.g., $Na_2SO_4$) 0% to about 5%; zeolite ($NaAlSiO_4$) about 15% to about 28%; sodium perborate (e.g., $NaBO_3.4H_2O$) 0% to about 20%; bleach activator (TAED or NOBS) about 0% to about 5%; enzymes (calculated as pure enzyme protein) 0.0001-0.1%; minor ingredients (e.g., perfume, optical brighteners) 0-3%.

13) Detergent compositions as described in compositions 1)-12) supra, wherein all or part of the linear alkylbenzenesulfonate is replaced by ($C_{12}$-$C_{18}$) alkyl sulfate.

14) A detergent composition formulated as a granulate having a bulk density of at least 600 g/L comprising ($C_{12}$-$C_{18}$) alkyl sulfate about 9% to about 15%; alcohol ethoxylate about 3% to about 6%; polyhydroxy alkyl fatty acid amide about 1% to about 5%; zeolite (e.g., $NaAlSiO_4$) about 10% to about 20%; layered disilicate (e.g., SK56 from Hoechst) about 10% to about 20%; sodium carbonate (e.g., $Na_2CO_3$) about 3% to about 12%; soluble silicate (e.g., $Na_2O$, $2SiO_2$) 0% to about 6%; sodium citrate about 4% to about 8%; sodium percarbonate about 13% to about 22%; TAED about 3% to about 8%; polymers (e.g., polycarboxylates and PVP) 0% to about 5%; enzymes (calculated as pure enzyme protein) 0.0001-0.1%; and minor ingredients (e.g., optical brightener, photobleach, perfume, suds suppressors) 0-5%.

15) A detergent composition formulated as a granulate having a bulk density of at least 600 g/L comprising ($C_{12}$-$C_{18}$) alkyl sulfate about 4% to about 8%; alcohol ethoxylate about 11% to about 15%; soap about 1% to about 4%; zeolite MAP or zeolite A about 35% to about 45%; sodium carbonate (as $Na_2CO_3$) about 2% to about 8%; soluble silicate (e.g., $Na_2O$, $2SiO_2$) 0% to about 4%; sodium percarbonate about 13% to about 22%; TAED 1-8%; carboxymethylcellulose (CMC) 0% to about 3%; polymers (e.g., polycarboxylates and PVP) 0% to about 3%; enzymes (calculated as pure enzyme protein) 0.0001-0.1%; and minor ingredients (e.g., optical brightener, phosphonate, perfume) 0-3%.

16) Detergent formulations as described in 1)-15) supra, which contain a stabilized or encapsulated peracid, either as an additional component or as a substitute for already specified bleach systems.

17) Detergent compositions as described supra in 1), 3), 7), 9), and 12), wherein perborate is replaced by percarbonate.

18) Detergent compositions as described supra in 1), 3), 7), 9), 12), 14), and 15), which additionally contain a manganese catalyst. The manganese catalyst for example is one of the compounds described in Rage et al. (1994) Nature 369:637-639.

19) Detergent composition formulated as a non-aqueous detergent liquid comprising a liquid nonionic surfactant such as, e.g., linear alkoxylated primary alcohol, a builder system (e.g., phosphate), an enzyme(s), and alkali. The detergent may also comprise anionic surfactant and/or a bleach system.

An AmyNEST polypeptide may be incorporated in concentrations conventionally employed in detergents. It is at present contemplated that, in the detergent composition, the enzyme may be added in an amount corresponding to 0.00001-1.0 mg (calculated as pure enzyme protein) of AmyNEST polypeptide per liter of wash liquor.

In another embodiment, other enzymes, such as 2,6-β-D-fructan hydrolase, can be incorporated in detergent compositions comprising an AmyNEST-related amylase and used for removal/cleaning of biofilm present on household and/or industrial textile/laundry.

The detergent composition may for example be formulated as a hand (manual) or machine (automatic) laundry detergent composition, including a laundry additive composition suitable for pre-treatment of stained fabrics and a rinse added fabric softener composition, or be formulated as a detergent composition for use in general household hard surface cleaning operations, or be formulated for manual or automatic dishwashing operations.

In a specific aspect, the detergent composition can comprise 2,6-β-D-fructan hydrolase in addition to an AmyNEST polypeptide, and one or more other cleaning enzymes, such as a protease, a lipase, a cutinase, a carbohydrase, a cellulase, a pectinase, a mannanase, an arabinase, a galactanase, another amylolytic enzyme, a xylanase, an oxidase, a laccase, and/or a peroxidase, and/or combinations thereof.

In general the properties of the chosen enzyme(s) should be compatible with the selected detergent, (e.g., pH-optimum, compatibility with other enzymatic and non-enzymatic ingredients, etc.), and the enzyme(s) should be present in effective amounts.

Proteases: Suitable proteases include those of animal, vegetable or microbial origin. Chemically modified or protein engineered mutants are included, as well as naturally processed proteins. The protease may be a serine protease or a metalloprotease, such as an alkaline microbial protease, a trypsin-like protease, or a chymotrypsin-like protease. Examples of alkaline proteases are subtilisins, especially those derived from *Bacillus*, e.g., subtilisin Novo, subtilisin Carlsberg, subtilisin 309, subtilisin 147, and subtilisin 168 (see, e.g., WO 89/06279). Examples of trypsin-like proteases are trypsin (e.g., of porcine or bovine origin), and *Fusarium* proteases (see, e.g., WO 89/06270 and WO 94/25583). Examples of useful proteases also include but are not limited to the variants described in WO 92/19729, WO 98/20115, WO 98/20116, and WO 98/34946. Commercially available protease enzymes include but are not limited to: ALCALASE®, SAVINASE®, PRIMASE™, DURALASE™, ESPERASE®, and KANNASE™ (Novo Nordisk A/S); MAXATASE®, MAXACAL™, MAXAPEM™, PROPERASE®, PURAFECT®, PURAFECT OXP™, FN2™, and FN3™ (Genencor International, Inc.).

Lipases: Suitable lipases include those of bacterial or fungal origin. Chemically modified, proteolytically modified, or protein engineered mutants are included. Examples of useful lipases include but are not limited to lipases from *Humicola* (synonym *Thermomyces*), e.g., from *H. lanuginosa* (*T. lanuginosus*) (see e.g., EP 258068 and EP 305216), from *H. insolens* (see e.g., WO 96/13580); a *Pseudomonas* lipase (e.g., from *P. alcaligenes* or *P. pseudoalcaligenes*; see, e.g., EP 218 272), *P. cepacia* (see e.g., EP 331 376), *P. stutzeri* (see e.g., GB 1,372,034), *P. fluorescens, Pseudomonas* sp. strain SD 705 (see e.g., WO 95/06720 and WO 96/27002), *P. wisconsinensis* (see e.g., WO 96/12012); a *Bacillus* lipase (e.g., from *B. subtilis*; see e.g., Dartois et al. *Biochemica et Biophysica Acta*, 1131: 253-360 (1993)), *Geobacillus* (formerly *Bacillus*) *stearothermophilus* (see e.g., JP 64/744992), or *B. pumilus* (see e.g., WO 91/16422). Additional lipase variants contemplated for use in the formulations include those described for example in: WO 92/05249, WO 94/01541, WO 95/35381, WO 96/00292, WO 95/30744, WO 94/25578, WO 95/14783, WO 95/22615, WO 97/04079, WO 97/07202, EP 407225, and EP 260105. Some commercially available lipase enzymes include LIPOLASE® and LIPOLASE ULTRA™ (Novo Nordisk A/S).

Polyesterases: Suitable polyesterases can be included in the composition, such as those described in, for example, WO 01/34899 and WO 01/14629.

Amylases: The compositions can be combined with other amylases, such as non-production enhanced α-amylase. These can include commercially available amylases, such as but not limited to DURAMYL®, TERMAMYL®, FUNGAMYL® and BAN™ (Novo Nordisk A/S); RAPIDASE® and PURASTAR® (from Genencor International, Inc.).

Cellulases: Cellulases can be added to the compositions. Suitable cellulases include those of bacterial or fungal origin.

Chemically modified or protein engineered mutants are included. Suitable cellulases include cellulases from the genera *Bacillus, Pseudomonas, Humicola, Fusarium, Thielavia, Acremonium*, e.g., the fungal cellulases produced from *Humicola insolens, Myceliophthora thermophila* and *Fusarium oxysporum* disclosed for example in U.S. Pat. Nos. 4,435, 307; 5,648,263; 5,691,178; 5,776,757; and WO 89/09259. Exemplary cellulases contemplated for use are those having color care benefit for the textile. Examples of such cellulases are cellulases described in for example EP 0495257, EP 0531372, WO 96/11262, WO 96/29397, and WO 98/08940. Other examples are cellulase variants, such as those described in WO 94/07998; WO 98/12307; WO 95/24471; PCT/DK98/ 00299; EP 531315; U.S. Pat. Nos. 5,457,046; 5,686,593; and 5,763,254. Commercially available cellulases include CELLUZYME® and CAREZYME® (Novo Nordisk A/S); CLAZINASE® and PURADAX HA® (Genencor International, Inc.); and KAC-500(B)™ (Kao Corporation).

Peroxidases/Oxidases: Suitable peroxidases/oxidases contemplated for use in the compositions include those of plant, bacterial or fungal origin. Chemically modified or protein engineered mutants are included. Examples of useful peroxidases include peroxidases from *Coprinus*, e.g., from *C. cinereus*, and variants thereof as those described in WO 93/24618, WO 95/10602, and WO 98/15257. Commercially available peroxidases include for example GUARDZYME™ (Novo Nordisk A/S).

The detergent enzyme(s) may be included in a detergent composition by adding separate additives containing one or more enzymes, or by adding a combined additive comprising all of these enzymes. A detergent additive, i.e. a separate additive or a combined additive, can be formulated e.g., as a granulate, a liquid, a slurry, etc. Exemplary detergent additive formulations include but are not limited to granulates, in particular non-dusting granulates, liquids, in particular stabilized liquids or slurries.

Non-dusting granulates may be produced, e.g., as disclosed in U.S. Pat. Nos. 4,106,991 and 4,661,452 and may optionally be coated by methods known in the art. Examples of waxy coating materials are poly(ethylene oxide) products (e.g., polyethyleneglycol, PEG) with mean molar weights of 1,000 to 20,000; ethoxylated nonylphenols having from 16 to 50 ethylene oxide units; ethoxylated fatty alcohols in which the alcohol contains from 12 to 20 carbon atoms and in which there are 15 to 80 ethylene oxide units; fatty alcohols; fatty acids; and mono- and di- and triglycerides of fatty acids. Examples of film-forming coating materials suitable for application by fluid bed techniques are given in, for example, GB 1483591. Liquid enzyme preparations may, for instance, be stabilized by adding a polyol such as propylene glycol, a sugar or sugar alcohol, lactic acid or boric acid according to established methods. Protected enzymes may be prepared according to the method disclosed in EP 238,216.

The detergent composition may be in any convenient form, e.g., a bar, a tablet, a powder, a granule, a paste, or a liquid. A liquid detergent may be aqueous, typically containing up to about 70% water, and 0% to about 30% organic solvent. Compact detergent gels containing about 30% or less water are also contemplated. The detergent composition can optionally comprise one or more surfactants, which may be non-ionic, including semi-polar and/or anionic and/or cationic and/or zwitterionic. The surfactants can be present in a wide range, from about 0.1% to about 60% by weight.

When included therein the detergent will typically contain from about 1% to about 40% of an anionic surfactant, such as linear alkylbenzenesulfonate, α-olefinsulfonate, alkyl sulfate (fatty alcohol sulfate), alcohol ethoxysulfate, secondary alkanesulfonate, α-sulfo fatty acid methyl ester, alkyl- or alkenylsuccinic acid, or soap.

When included therein, the detergent will usually contain from about 0.2% to about 40% of a non-ionic surfactant such as alcohol ethoxylate, nonylphenol ethoxylate, alkylpolyglycoside, alkyldimethylamineoxide, ethoxylated fatty acid monoethanolamide, fatty acid monoethanolamide, polyhydroxy alkyl fatty acid amide, or N-acyl-N-alkyl derivatives of glucosamine ("glucamides").

The detergent may contain 0% to about 65% of a detergent builder or complexing agent such as zeolite, diphosphate, triphosphate, phosphonate, carbonate, citrate, nitrilotriacetic acid, ethylenediaminetetraacetic acid (EDTA), diethylenetriaminepentaacetic acid, alkyl- or alkenylsuccinic acid, soluble silicates or layered silicates (e.g., SKS-6 from Hoechst).

The detergent may comprise one or more polymers. Exemplary polymers include carboxymethylcellulose (CMC), poly (vinylpyrrolidone) (PVP), poly(ethylene glycol) (PEG), poly (vinyl alcohol) (PVA), poly(vinylpyridine-N-oxide), poly (vinylimidazole), polycarboxylates e.g., polyacrylates, maleic/acrylic acid copolymers), and lauryl methacrylate/ acrylic acid copolymers.

The enzyme(s) of the detergent composition may be stabilized using conventional stabilizing agents, e.g., as polyol (e.g., propylene glycol or glycerol), a sugar or sugar alcohol, lactic acid, boric acid, or a boric acid derivative (e.g., an aromatic borate ester), or a phenyl boronic acid derivative (e.g., 4-formylphenyl boronic acid). The composition may be formulated as described in WO 92/19709 and WO 92/19708.

It is at present contemplated that in the detergent compositions, the AmyNEST-related polypeptides may be added in an amount corresponding to about 0.01 to about 100 mg of enzyme protein per liter of wash liquor (e.g., about 0.05 to about 5.0 mg of enzyme protein per liter of wash liquor or 0.1 to about 1.0 mg of enzyme protein per liter of wash liquor).

4.2 Cleaning Compositions

In the detergent applications, an AmyNEST polypeptide is usually used in a liquid composition containing propylene glycol. The enzyme is solubilized in for example in propylene glycol by mixing in a 25% volume/volume propylene glycol solution containing 10% calcium chloride.

An AmyNEST polypeptide thereof discussed herein can be formulated in detergent compositions for use in cleaning dishes or other cleaning compositions. These can be powders, gels, or liquids. The compositions can comprise the enzyme alone, or with other amylolytic enzymes and/or with other cleaning enzymes or bleach activating enzymes, and other components common to cleaning compositions.

Thus, a dishwashing detergent composition can comprise a surfactant. The surfactant may be anionic, non-ionic, cationic, amphoteric or a mixture of these types. The detergent can contain 0% to about 90% by weight of a non-ionic surfactant, such as low- to non-foaming ethoxylated propoxylated straight-chain alcohols.

The detergent composition may contain detergent builder salts of inorganic and/or organic types. The detergent builders may be subdivided into phosphorus-containing and non-phosphorus-containing types. The detergent composition usually contains about 1% to about 90% of detergent builders. Examples of phosphorus-containing inorganic alkaline detergent builders, when present, include the water-soluble salts, especially alkali metal pyrophosphates, orthophosphates, and polyphosphates. An example of phosphorus-containing organic alkaline detergent builder, when present, includes the water-soluble salts of phosphonates. Examples of non-phosphorus-containing inorganic builders, when present, include water-soluble alkali metal carbonates, borates, and silicates, as well as the various types of water-insoluble crystalline or amorphous alumino silicates, of which zeolites are the best-known representatives.

Examples of suitable organic builders include the alkali metal; ammonium and substituted ammonium; citrates; succinates; malonates; fatty acid sulphonates; carboxymethoxy succinates; ammonium polyacetates; carboxylates; polycarboxylates; aminopolycarboxylates; polyacetyl carboxylates; and polyhydroxysulphonates.

Other suitable organic builders include the higher molecular weight polymers and co-polymers known to have builder properties, for example appropriate polyacrylic acid, polymaleic and polyacrylic/polymaleic acid copolymers, and their salts.

The cleaning composition may contain bleaching agents of the chlorine/bromine-type or the oxygen-type. Examples of inorganic chlorine/bromine-type bleaches are lithium, sodium or calcium hypochlorite, and hypobromite, as well as chlorinated trisodium phosphate. Examples of organic chlorine/bromine-type bleaches are heterocyclic N-bromo- and N-chloro-imides such as trichloroisocyanuric, tribromoisocyanuric, dibromoisocyanuric, and dichloroisocyanuric acids, and salts thereof with water-solubilizing cations such as potassium and sodium. Hydantoin compounds are also suitable.

The cleaning composition may contain oxygen bleaches, for example in the form of an inorganic persalt, optionally with a bleach precursor or as a peroxy acid compound. Typical examples of suitable peroxy bleach compounds are alkali metal perborates, both tetrahydrates and monohydrates, alkali metal percarbonates, persilicates, and perphosphates. Exemplary activator materials are TAED, and glycerol triacetate. Enzymatic bleach activation systems may also be present in the formulation, e.g., such as perborate or percarbonate, glycerol triacetate and perhydrolase (see, e.g., WO 2005/056783).

The cleaning composition may be stabilized using conventional stabilizing agents for the enzyme(s), e.g., a polyol such as, e.g., propylene glycol, a sugar or a sugar alcohol, lactic acid, boric acid, or a boric acid derivative (e.g., an aromatic borate ester).

The cleaning composition may also contain other conventional detergent ingredients, e.g., deflocculant material, filler material, foam depressors, anti-corrosion agents, soil-suspending agents, sequestering agents, anti-soil redeposition agents, dehydrating agents, dyes, bactericides, fluorescers, thickeners, and perfumes.

Although the present compositions and methods have been described with reference to the details below, it would be understood that various modifications can be made.

4.3 Methods of Assessing Detergent Compositions

Numerous α-amylase cleaning assays exist. Exemplary description of testing cleaning includes the following.

A "swatch" is a piece of material such as a fabric that has a stain applied thereto. The material can be, for example, fabrics made of cotton, polyester or mixtures of natural and synthetic fibers. The swatch can further be paper, such as filter paper or nitrocellulose, or a piece of a hard material such as ceramic, metal, or glass. For amylases, the stain is starch based, but can include blood, milk, ink, grass, tea, wine, spinach, gravy, chocolate, egg, cheese, clay, pigment, oil, or mixtures of these compounds.

A "smaller swatch" is a section of the swatch that has been cut with a single hole punch device, or has been cut with a custom manufactured 96-hole punch device, where the pattern of the multi-hole punch is matched to standard 96-well microtiter plates, or the section has been otherwise removed from the swatch. The swatch can be of textile, paper, metal, or other suitable material. The smaller swatch can have the stain affixed either before or after it is placed into the well of a 24-, 48- or 96-well microtiter plate. The "smaller swatch" can also be made by applying a stain to a small piece of material. For example, the smaller swatch can be a stained piece of fabric ⅝-inches or 0.25-inches in diameter. The custom manufactured punch is designed in such a manner that it delivers 96 swatches simultaneously to all wells of a 96-well plate. The device allows delivery of more than one swatch per well by simply loading the same 96-well plate multiple times. Multi-hole punch devices can be conceived of to deliver simultaneously swatches to any format plate, including but not limited to 24-well, 48-well, and 96-well plates. In another conceivable method, the soiled test platform can be a bead made of either metal, plastic, glass, ceramic, or other suitable material that is coated with the soil substrate. The one or more coated beads are then placed into wells of 96-, 48-, or 24-well plates or larger formats, containing suitable buffer and enzyme. In this case, supernatant can be examined for released soil either by direct absorbance measurement or after a secondary color development reaction. Analysis of the released soil might also be taken by mass spectral analysis. A further microscreening assay can be to deliver and secure a swatch, for example an indigo dyed denim, to a well of a multi-well plate, and add particles such as sand or larger particles such as for example garnet sieved to include particle 6 to 8, or 9 gauge, and agitate the plate so as to cause abrasion of the swatch by the added particles. This assay has found use in the assessment of cellulases in stone washing applications. The effectiveness of the enzyme can be judged by either color release (e.g., released indigo is dissolved in dimethylsulfoxide and absorbance at $A_{600}$ nm is measured) to the reaction buffer or by reflectance measurements of the abraded swatch.

When, for example, untreated BMI (blood/milk/ink) swatches are washed in detergent without bleach, a large portion of the ink is released even without the help of a protease. Adding a protease leads to a small increase in ink release, which can be hard to quantify over the large background. The present compositions and methods provide a treatment protocol that allows one to control the degree of fixation of a stain. As a result, it is possible to produce swatches that, for example, release varying amounts of stain when washed in the absence of the enzyme being tested. The use of fixed swatches leads to a dramatic improvement of the signal-to-noise ratio in the wash assays. Furthermore, by varying the degree of fixation, one can generate stains that give optimum results under the various cleaning conditions.

Swatches having stains of known "strength" on various types of material are commercially available (EMPA, St. Gallen, Switzerland; wfk—Testgewebe GmbH, Krefeld Germany; or Center for Test Materials, Vlaardingen, The Netherlands) and/or can be made by the practitioner (Morris and Prato, Textile Research Journal 52(4): 280 286 (1982)). Other test swatches include but are not limited to blood/milk/ink (BMI) stain(s) on a cotton-containing fabric, a spinach stain on a cotton-containing fabric, or grass on a cotton-containing fabric, and chocolate/milk/soot on a cotton-containing fabric.

A BMI stain can be fixed to cotton with 0.0003% to 0.3% hydrogen peroxide. Other combinations include grass or spinach fixed with 0.001% to 1% glutaraldehyde, gelatin and Coomassie stain fixed with 0.001% to 1% glutaraldehyde, or chocolate, milk and soot fixed with 0.001% to 1% glutaraldehyde.

The swatch can also be agitated during incubation with the enzyme and/or detergent formulation. Wash performance data is dependent on the orientation of the swatches in the wells (horizontal versus vertical), particularly in the 96-well plate. This would indicate that mixing was insufficient during the incubation period. Although there are a number of ways to ensure sufficient agitation during incubation, a plate holder in which the microtiter plate is sandwiched between two plates of aluminum can be constructed. This can be as simple as placing, for example, an adhesive plate sealer over the wells then clamping the two aluminum plates to the 96-well plate with any type of appropriate, commercially available clamps. It can then be mounted in a commercial incubator shaker. Setting the shaker to about 400 rpm results in very efficient mixing, while leakage or cross-contamination is efficiently prevented by the holder.

Trinitrobenzenesulfonic acid (TNBS) can be used to quantify the concentration of amino groups in the wash liquor. This can serve as a measure of the amount of protein that was removed from the swatch (see e.g., Cayot and Tainturier, Anal. Biochem. 249: 184-200 (1997)). However, if a detergent or an enzyme sample leads to the formation of unusually small peptide fragments (for example, from the presence of peptidases in the sample), then one will obtain a larger TNBS signal, i.e., more "noise".

Another means of measuring wash performance of blood/milk/ink or other stain is based on ink release. Proteolysis of protein on the swatches leads to the release of ink particles which can be quantified by measuring the absorbance of the wash liquor. The absorbance can be measured at any wavelength between 350 and 800 nm. The absorbance is measured at 410 nm or 620 nm. The wash liquor can also be examined to determine the wash performance on stains containing grass, spinach, gelatin or Coomassie stain. Exemplary wavelengths for these stains include 670 nm for spinach or grass and 620 nm for gelatin or Coomassie. For example, an aliquot of the wash liquor (typically 100-150 µL from a 96-well microplate, for example) is removed and placed in a cuvette or multiwell microplate. This is then placed in a spectrophotometer and the absorbance is read at an appropriate wavelength.

The system can also be used to determine an enhanced enzyme and/or detergent composition for dish washing, for example, using a blood/milk/ink stain on a suitable substrate such as cloth, plastic or ceramic.

In one aspect, the BMI stain is fixed to cotton by applying 0.3% hydrogen peroxide to the BMI/cotton swatch for 30 minutes at 25° C. or by applying 0.03% hydrogen peroxide to the BMI/cotton swatch for 30 minutes at 60° C. Smaller swatches of approximately 0.25-inches are cut from the BMI/cotton swatch and placed in the wells of a 96-well microtiter plate. Into each well, a known mixture of a detergent composition and an enzyme is placed. After placing an adhesive plate sealer onto the top of the microtiter plate, the microtiter plate is clamped to an aluminum plate and agitated on an orbital shaker at approximately 250 rpm for about 10 to 60 minutes. At the end of this time, the supernatants are transferred to wells in a new microtiter plate and the absorbance of the ink at 620 nm is measured. This can be similarly tested with spinach stains or grass stains fixed to cotton by applying 0.01% glutaraldehyde to the spinach/cotton swatch or grass/cotton swatch for 30 minutes at 25° C. The same can be done with chocolate, milk, and/or soot stains.

The present application is organized into a number of sections for ease of reading; however, the reader will appreciate that statements made in one section may apply to other sections. In this manner, the headings used for different sections of the disclosure should not be construed as limiting.

In order to further illustrate the compositions and methods, and advantages thereof, the following specific examples are given with the understanding that they are illustrative rather than limiting.

EXAMPLES

Example 1

Isolation of *Nesterenkonia xinjianensis* Strain B4.2S6

*Nesterenkonia xinjianensis* strain B4.2S6 was isolated from an alkaline (pH 10.5, 27.5° C.) and saline (conductivity 25.8 mS·cm-1) lake sediment by cultivation on moderate halophile medium (MHM), pH7-7.5, 30° C., consisting of NaCl, 10%; yeast extract, 1%; glucose, 0.1%; peptone, 0.5%; agar, 1.8%. The organism formed pale yellow colonies.

Example 2

Identification of *N. xinjianensis* Strain B4.2S6

*N. xinjianensis* strain B4.2S6 was grown on GAM agar (see Example 3) and sent to BaseClear (Leiden, The Netherlands) for partial 16S rRNA gene sequencing. Sequencing was performed using standard PCR primers, 16S-500-F1 and 16S-500-R1 provided by BaseClear. The 440 bp partial sequence is shown in SEQ ID NO: 1. A BLAST search revealed that the 440 bp fragment was 100% identical to a similar sequence from strain YIM 70097, the Type Strain of *N. xinjiangensis* (Wen-Jun Li et al. (2004) *Int. J. Syst. Evol. Microbiol.* 54:837-41). These data demonstrated that the cloned amylase corresponded to that of *N. xinjiangensis*.

Example 3

Cultivation of *N. xinjiangensis* B4.2S6

The *N. xinjianensis* strain B4.2S6 bacteria were cultivated at 35° C. on moderate halophile medium (MHM) pH 7-7.5 or alkaline GAM medium pH 10-10.5, as described, below.

MHM Medium (g/L)

| | |
|---|---|
| NaCl | 100.0 |
| Yeast extract | 10.0 |
| Glucose | 1.0 |
| Peptone | 5.0 |
| Agar | 18.0 |

GAM Medium (g/L)
Solution A

| | |
|---|---|
| Glucose | 10.0 |
| Peptone (Difco) | 5.0 |
| Yeast extract | 5.0 |
| $K_2HPO_4$ | 1.0 |
| $MgSO_4 \cdot 7H_2O$ | 0.4 | dissolved in 500 ml deionised water and sterilized by autoclaving.

Solution B

| | |
|---|---|
| NaCl | 40.0 |
| $Na_2CO_3$ | 10.0 | dissolved in 500 ml deionised water and sterilized by autoclaving.

After sterilization and cooling, solution A and solution B were mixed and distributed into shake flasks. Solid medium contained 20.0 g/L agar. Good growth was obtained after 72 h cultivation. Agar plates provided pure cultures of pale yellow colonies.

Example 4

Identification of *N. xinjiangensis* B4.2S6 α-amylase from an Expression Library Cells of *N. xinjiangensis* B4.2S6 were cultivated on an alkaline medium, using methods similar those described in Duckworth et al. (1996) *FEMS Microbiology Letters* 19:181-91. Genomic DNA was prepared using MasterPure Gram Positive DNA purification Kit (Epicentre; Madison, Wis., USA) using the manufacturer's protocol.

Genomic DNA of *N. xinjiangensis* B4.256 was used by Eurofins Medigenomix GmbH (Fraunhoferstrasse 22 D-82152 Martinsried, Del.) for the construction of an expression library. Fragments of 3-5 kb were obtained by random shearing of genomic DNA of *N. xinjiangensis* B4.2S6. The fragments were cloned into low copy number vector pRANGER-BTB3-Cat (FIG. 1, Lucigen Corporation, Middleton, Wis., USA, GenBank Accession No. DQ058731). The arabinose promoter drove transcription of the inserted genes (so long as there was no terminator present in the insert, and only in one orientation). Translation depended on the native RBS/Start codon of the gene(s) present in the cloned inserts. The vector was first modified for TA Cloning by Medigenomix (Ebersberg, Del.) by insertion of a EcoRV restriction site in the MCS, adding single 3'-thymidine overhangs and insertion of three stop codons (in three frames) after the T/A insertion site and before the terminator on the vector.

Ligation mixtures were transformed into electrocompetent TOP10 *E. coli* cells (Invitrogen Corporation, Carlsbad, Calif., USA) and plated on RBB agar plates. These agar plates contained 10 g yeast extract, 16 g tryptone, 5 g NaCl, 15 g agar, 25 mg chloramphenicol, and 5 g starch dyed with Remazol brilliant blue R (Fluka/Sigma-Aldrich; Zwijndrecht, The Netherlands) per liter. An *E. coli* clone that formed a clearing zone on the RBB plate, indicating the presence of an amylase gene, was selected for further study. The insert of this starch halo-positive clone was sequenced by BaseClear (Einsteinweg; Leiden, The Netherlands) using DNA primers pRANGER-FW (SEQ ID NO: 2) and pRANGER-RV (SEQ ID NO: 3), which hybridize to the pRANGER vector. By using three internal DNA primers (based on DNA sequences retrieved using the aforementioned pRANGER primers) the DNA sequence of the entire insert was determined. Analysis revealed the presence of the *N. xinjiangensis* B4.2S6 α-amylase gene (SEQ ID NO: 7). The deduced amino acid sequence of the mature α-amylase protein is shown as SEQ ID NO: 9.

Example 5

Characterization of the *N. xinjiangensis* α-amylase Gene and Protein

The *N. xinjiangensis* α-amylase gene encodes a precursor protein of 724 amino acids (SEQ ID NO: 9). The precursor protein comprises a signal peptide of 24 amino acids (SEQ ID NO: 10) and a mature protein (AmyNEST) of 700 amino acids (SEQ ID NO: 11). A BLAST search revealed that AmyNEST has rather low identity to any known amylases. The closest homologue is the α-amylase from *Bacillus* sp. 195 (SEQ ID NO: 18), which shares 56% identity with AmyNEST.

Figure 2:
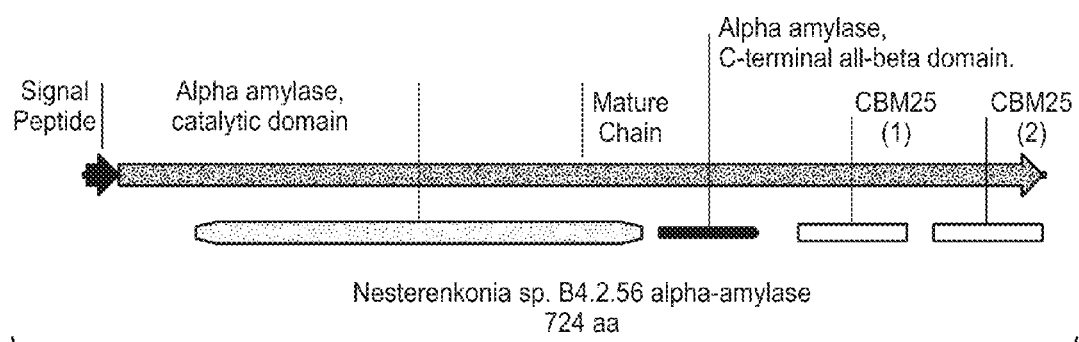
FIG. 2 is a schematic showing the organization of AmyNEST protein depicting the catalytic domain and two carbohydrate-binding modules (CBM).

Comparison of AmyNEST with the α-amylase from *Bacillus* sp. 195 suggested that AmyNEST has a catalytic domain and two carbohydrate binding modules with an organisation as shown in FIG. 2. The two carbohydrate binding modules (CBM) both belong to the CBM 25 superfamily and are in tandem at the C-terminal end of the molecule separated by a linker portion of 17 amino acids [i.e., DPCEAQPAPGEDPDLTV (SEQ ID NO: 19)]. These CBMs are designated CBM 25(1) (SEQ ID NO: 12) and CBM 25(2) (SEQ ID NO: 13), which share 60% sequence identity. The CBM likely contribute to starch binding features and the ability to degrade raw starch (see, e.g., Sumitani, J. et al. (2000) New type of starch-binding domain: the direct repeat motif in the C-terminal region of *Bacillus* sp. no. 195 α-amylase contributes to starch binding and raw starch degrading. *Biochem. J.* 350(PT 2):477-84).

Example 6

Small-Scale Expression of *N. xinjiangensis* amylase

Two shake flasks (250 ml) containing 100 ml GAM medium were inoculated (1:10) with 10 ml seed culture and incubated at 35° C. and 220 rpm in a shaking incubator for 24 h to serve as inoculum for the starch fermentation. The amylase production medium (sGAM) consisted of modified GAM medium with glucose replaced by soluble starch (10 g/L) and reduced peptone at 1 g/L. Shake flasks (250 ml) containing 100 ml sGAM broth were inoculated with 10 ml of inoculum culture and incubated at 35° C. and 220 rpm in a shaking incubator for 48 h. Amylase production medium (2.7 L) was harvested by centrifugation (10° C.), first at 4700 rpm (Sigma) and then at 10,000 rpm (Sorval) to remove remaining cells. The supernatant was stored at −80° C. until concentrated. To reduce degradation by proteases, three tablets of Protease Inhibitor Cocktail (i.e., Roche, "Complete") were added. The supernatant was concentrated (on ice) by continuous recirculation membrane filtration (5K MW cut-off), using 200 cm$^2$ active membrane area (Vivaflow200) from 2700 ml to 70 ml. During the UF process, additional tablets of Protease Inhibitor Cocktail were added. The concentrate was stored at −80° C.

Figure 3:
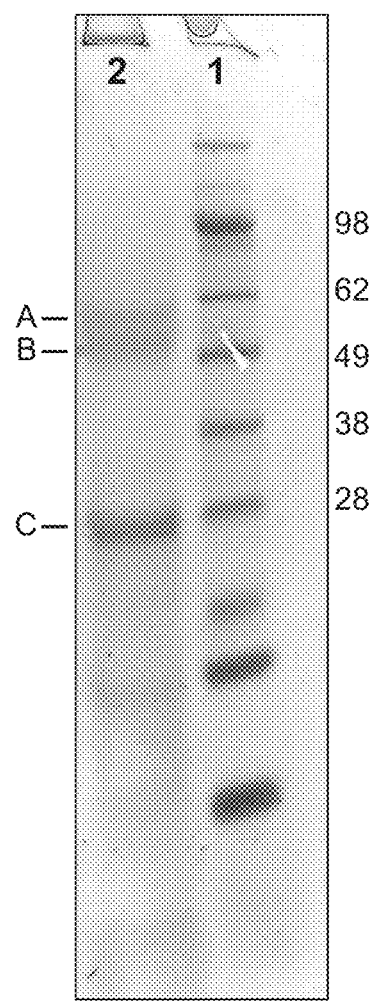
FIG. 3 is an image of a Coomassie Brilliant Blue-stained SDS-PAGE gel showing three major bands at 60, 50, and 27 kDa.

SDS-PAGE analysis was performed using Invitrogen NuPAGE Novex Bis-Tris gels in MES SDS running buffer. 50 μL sample was diluted with 25 μL 0.5 N HCl. After standing on ice for 5 min, 25 μL sample buffer was added and the samples were heated at 95° C. for 5 min. The samples were briefly chilled on ice and then subjected to centrifugation before loading 30, 40 or 10 μL to the gel slots. Electrophoresis was performed at 100 V (constant voltage) and the protein bands visualized with Coomassie Brilliant Blue (Invitrogen). Three major bands were visible at 60, 50 and 27 kDa (FIG. 3).

The presence of amylase in the broth concentrate was confirmed using an agarose gel diffusion assay that utilized soluble starch as a substrate. Aliquots of 80, 40, 20 or 10 μL of concentrate were placed in wells punched in the agarose and incubated overnight at 35° C. in a high humidity environment. Amylase activity around the wells was visualized by flooding the agarose plates with iodine solution (KI/I). Clearing zones or halos around the wells indicated the presence of amylase in *N. xinjiangensis* B4.2S6 broth concentrate. Similar halos were obtained using RBB starch as substrate. Skim milk plates exhibited no clearing zones indicating the absence of proteases.

Example 7

Large-Scale Expression of *N. xinjiangensis* amylase

Figure 4:
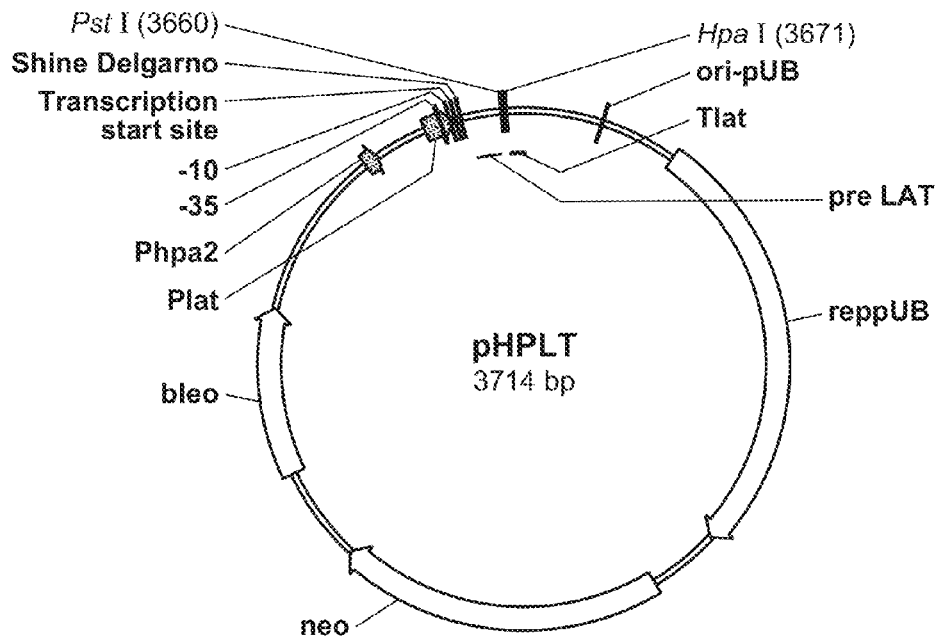
FIG. 4 is a plasmid map of pHPLT.

To express large quantities of *N. xinjiangensis* α-amylase in *Bacillus subtilis*, a construct was made by using the pHPLT vector. For expression studies, the mature coding sequence was N-terminal truncated by deleting the first 42 DNA codons and substituting the Serine at position 43 with an Alanine. The *N. xinjiangensis* α-amylase mature DNA fragment was cloned in the pHPLT vector (Solingen et al. (2001) *Extremophiles* 5:333-41; see FIG. 4), by using the unique PstI and HpaI restriction sites. The pHPLT expression vector contains the *B. licheniformis* LAT promoter (Plat) followed by PstI and HpaI restriction sites for cloning AmyNEST, and additional elements from pUB110 (McKenzie et al. (1986) *Plasmid* 15:93-103) including a replicase gene (reppUB), a neomycin/kanamycin resistance gene (neo) and a bleomycin resistance marker (bleo). A map of the pHPLT-AmyNEST plasmid is shown in FIG. 5.

To prepare genomic DNA from *N. xinjiangensis* B4.2S6, 1 ml cell pellet of overnight grown culture (Tryptic Soy Broth at 37° C.) was used as a source of genetic material. Genomic DNA was prepared using MasterPure Gram Positive DNA purification Kit from Epicentre (Epicentre; Madison, Wis., USA) following the manufacturer's protocol. The *N. xinjiangensis* B4.2S6 α-amylase gene was amplified by PCR from the genomic DNA using a MJ Research PTC-200 thermocycler with Phusion High Fidelity DNA polymerase (Finnzymes OY, Espoo, FN) according to the manufacturer's instructions, and using an annealing temperature of 55° C. The two primers used were: pHPLT-AmyNest-Fw (SEQ ID NO: 14) and pHPLT-AmyNest-Rv (SEQ ID NO: 15).

The resulting PCR fragment was digested with the restriction enzymes PstI and HpaI, and incubated in the presence of T4 DNA ligase along with pHPLT pDNA (50 ng/μL range, digested with PstI and HpaI restriction enzymes), according to the instructions of the supplier (Roche Applied Science, Indianapolis, Ind., USA). The ligation mixture was transformed into *B. subtilis* strain SC6.1 (ΔaprE, ΔnprE, oppA, ΔspoIIE, degUHy32, ΔamyE::[xylR,pxylA-comK]), as described in U.S. Patent Publication US20020182734 (International Publication WO 02/14490). The transformation was plated on DIFCO™ Heart Infusion Agar plates containing 10 mg/L Neomycin and 0.5% Starch dyed with Remazol brilliant blue R. A starch-halo-positive colony was evaluated for the presence of the *N. xinjiangensis* α-amylase gene in pHPLT using colony PCR and sequencing. For colony PCR, the *B. subtilis* transformant was resuspended in 100 μL of sterile water of which 1 μL was used in a PCR reaction containing Invitrogen Platinum Taq DNA Polymerase High Fidelity PCR system, and two primers pHPLT-F1 primer (SEQ ID NO: 16) and pHPLT-R1 primer (SEQ ID NO: 17).

The cycling conditions were 95° C. for 2 minutes for a single cycle; followed by 95° C. for 30 seconds, 55° C. for 1 minute, and 68° C. for 2 minutes, for a total of 25 cycles; followed by 5 minutes at 68° C. for one final cycle. The PCR product was sequenced at BaseClear using primers pHPLT-F1 (SEQ ID NO: 16) and pHPLT-R1 (SEQ ID NO: 17) and the primers Nest-Insert3-RV (SEQ ID NO: 4), Nest-Insert3-FW (SEQ ID NO: 5), and Nest-add-Fw (SEQ ID NO: 6). Sequence analysis confirmed the presence of the *N. xinjiangensis* α-amylase gene open reading frame in the pHPLT vector (i.e., pHPLT-AmyNEST; see FIG. 5).

Selective growth of *B. subtilis* transformants harboring the pHPLT-AmyNest vector was performed in shake flasks containing 25 ml MBD medium (a MOPS based defined medium) containing 5 mM $CaCl_2$ and 10 mg/L Neomycin. MBD medium was prepared according to Neidhardt et al. [(1974) *J. Bacteriol.* 119:736-47], with modifications. In particular, $NH_4Cl_2$, $FeSO_4$, and $CaCl_2$ were omitted from the base medium, 3 mM $K_2HPO_4$ was used, and the base medium was supplemented with 60 mM urea, 75 g/L glucose, and 1% soytone. The micronutrients were made up as a 100× stock solution containing in one liter, 400 mg $FeSO_4.7H_2O$, 100 mg $MnSO_4.H_2O$, 100 mg $ZnSO_4.7H_2O$, 50 mg $CuCl_2.2H_2O$, 100 mg $CoCl_2.6H_2O$, 100 mg $NaMoO_4.2H_2O$, 100 mg $Na_2B_4O_7.10H_2O$, 10 ml of 1M $CaCl_2$, and 10 ml of 0.5 M sodium citrate. Growth resulted in the production of secreted *N. xinjiangensis* α-amylase with starch hydrolyzing activity.

The α-amylase activity of AmyNEST culture supernatant from the transformants grown on MBD medium described above was determined using the Ceralpha method (Megazyme International, IR), which was modified for use in 96-well microtiter plate. 25 μl blocked p-nitrophenyl maltoheptaoside (i.e., BPNPG7) substrate, 5.45 mg/mM Amylase HR Reagent (Megazyme International; Catalogue Number R-AMHR4) was added to each well and pre-equilibrated for 10 minutes at a desired temperature, in this case 25° C. 25 μl of culture supernatant was diluted in 50 mM MOPS buffer pH 7.15, which additionally contained 50 mM NaCl and 0.1 mM $CaCl_2$, and the diluted culture supernatant was added to the wells and mixed with the substrate. The plates were incubated at the desired temperature with shaking at 650 rpm for 30 minutes in an incubator (iEMS, Labsystems), and the reaction was terminated by the addition of 50 μl 200 mM boric acid/NaOH (pH 10.2) solution into each well. The measured absorbance at 400 nm directly related to the level of α-amylase in the diluted samples.

Example 8

Cleaning Performance of AmyNEST

Culture supernatant from the pHPLT-AmyNest vector transformed cells grown in MBD medium (Example 5) was analyzed for activity in a 96-well CS28-orange-dyed-rice-starch-soiled-fabric-swatch micro-applications cleaning assay. Using a fabric punch, ¼-inch discs were cut from CS28 colored rice starch stained fabric swatches. This starch includes a bound indicator dye to facilitate tracking (Test Fabrics Cat. No. CS-28; Center for Test Materials, Vlaardingen, The Netherlands). Two of these discs were placed in each well of a flat-bottomed 96-well assay plates.

Figure 6:
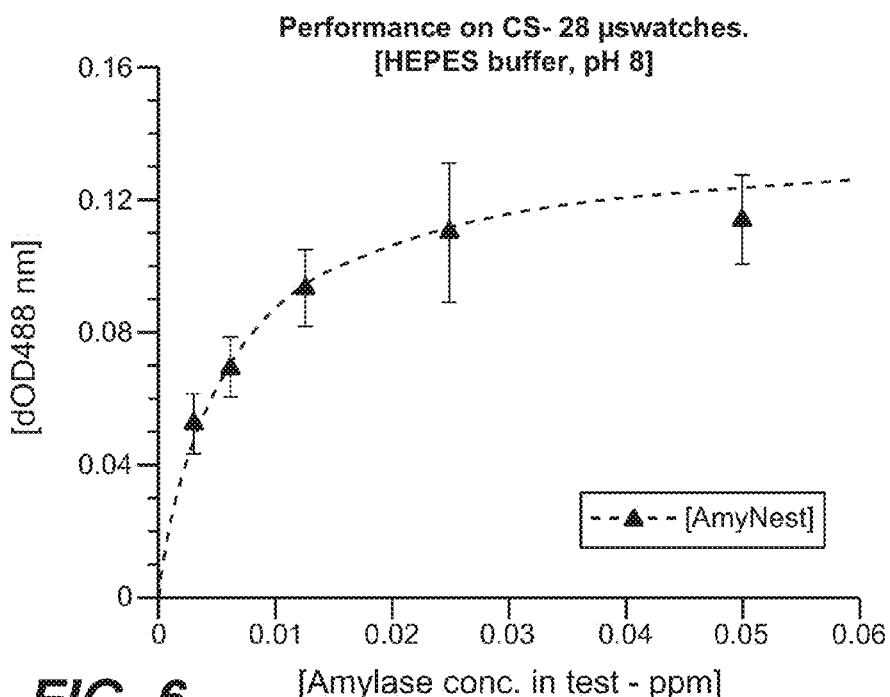
FIG. 6 shows the cleaning performance of AmyNEST on CS-28 rice-starch microswatches at pH 8 (HEPES buffer).
Figure 7:
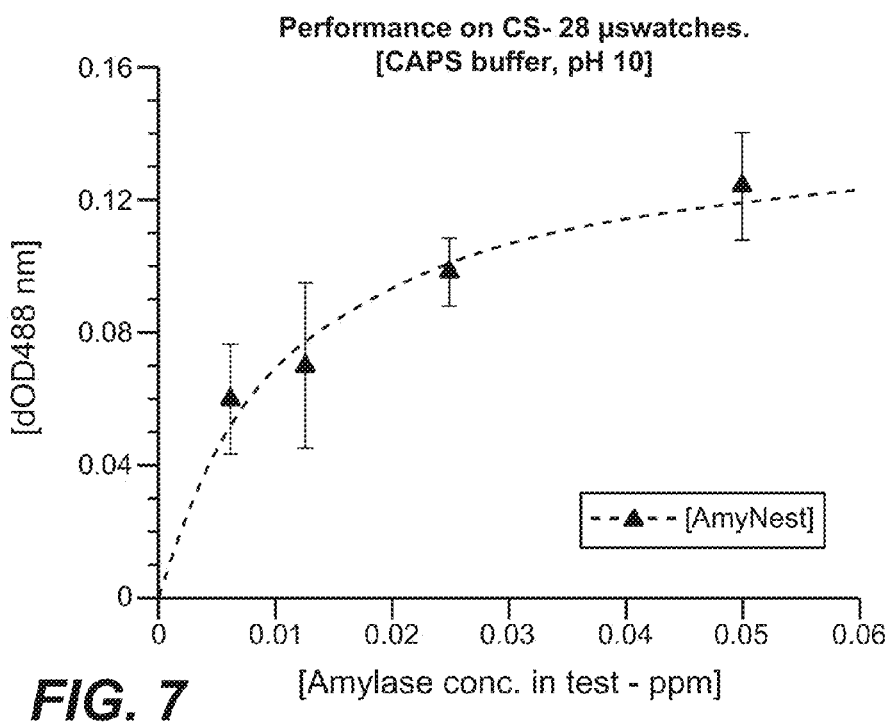
FIG. 7 shows the cleaning performance of AmyNEST on CS-28 rice-starch microswatches at pH 10 (CAPS buffer).

For the α-amylase cleaning assay, a preselected buffer was added to the wells of an assay plate and equilibrated to a preselected temperature. For initial testing, the buffers used were 25 mM HEPES (pH 8.0) or 25 mM CAPS (pH 10.0). additionally containing 2 mM $CaCl_2$ and 0.005% TWEEN 80. 190 μL or 180 μL of buffer was added to the wells and allowed to equilibrate at 40° C., then 10 or 20 μL of diluted culture supernatant (final amylase concentration of 0 ppm to 2 ppm) was added to selected wells. The plates were incubated at 40° C. with shaking at 1150 rpm for 1 hour. Enzyme cleaning performance was based on the amount of enzyme-dependent color released into the wash liquor. Color release was quantified spectrophotometrically at 488 nm by the transfer of 100 μL final wash liquor to a fresh microtiter plate. The data were normalized to a control reaction in which the amylase enzyme was not present) and plotted with the aid of GRAFIT from Erithicus Software. The data points were fitted with the Langmuir isotherm-fitting algorithm, which takes the same form as the Michaelis-Menten fitting algorithm. The results of this assay demonstrated that AmyNEST is highly efficient at removing starchy stains from textile swatches at 40° C. at both pH 8.0 and pH 10.0 (FIGS. 6 and 7, respectively).

All references cited herein are herein incorporated by reference in their entirety for all purposes.

What is claimed is:

1. An isolated α-amylase polypeptide comprising an amino acid sequence having at least 85% amino acid sequence identity to the amino acid sequence of SEQ ID NO: 11, wherein the polypeptide is a variant polypeptide comprising a man-made amino acid substitution, insertion, or deletion.

2. The isolated polypeptide of claim 1, having at least 90% amino acid sequence identity to the amino acid sequence of SEQ ID NO: 11.

3. The isolated polypeptide of claim 2, having at least 95% amino acid sequence identity to the amino acid sequence of SEQ ID NO: 11.

4. The isolated polypeptide of claim 1 comprising the amino acid sequence of carbohydrate binding module (CBM) 25(1) (SEQ ID NO: 12) and/or the amino acid sequence of CBM 25(2) (SEQ ID NO: 13).

5. The isolated polypeptide of claim 4 comprising the amino acid sequence of CBM 25(1) and the amino acid sequence of CBM 25(2) separated by a linker having the amino acid sequence of SEQ ID NO: 19.

6. The isolated polypeptide of claim 1 having alpha-amylase activity.

7. A composition comprising the polypeptide of claim 1.

8. The composition of claim 7, wherein the composition is effective for removing starchy stains from laundry, dishes, or textiles.

9. The composition of claim 7, further comprising a surfactant.

10. The composition of claim 7, wherein the composition is a detergent composition.

11. The composition of claim 7, wherein the composition is a laundry detergent or a laundry detergent additive.

12. The composition of claim 7, wherein the composition is manual or automatic dishwashing detergent.

13. A method for removing a starchy stain from a surface, comprising
    incubating the surface in the presence of a aqueous composition comprising an effective amount of a polypeptide of claim 1,
    allowing the polypeptide to hydrolyse starch components present in the starchy stain to produce smaller starch-derived molecules that dissolve in the aqueous composition,
    thereby removing the starchy stain from the surface.

14. The method of claim 13, wherein the aqueous composition further comprises a surfactant.

15. The method of claim 13, wherein the surface is a textile surface.

16. The method of claim 13, wherein the surface is on dishes.

17. The method of claim 13, wherein the surface is a soiled hard surface.

18. An expression vector comprising an isolated polynucleotide encoding a polypeptide of claim 1.

19. A host cell comprising the expression vector of claim 18.

* * * * *